United States Patent
Bora et al.

(10) Patent No.: US 8,780,439 B2
(45) Date of Patent: Jul. 15, 2014

(54) PLASMON RESONANT CAVITIES IN VERTICAL NANOWIRE ARRAYS

(75) Inventors: Mihail Bora, Livermore, CA (US);
Tiziana C. Bond, Livermore, CA (US);
Benjamin J. Fasenfest, Union City, CA (US); Elaine M. Behymer, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 210 days.

(21) Appl. No.: 13/410,226

(22) Filed: Mar. 1, 2012

(65) Prior Publication Data
US 2012/0224255 A1    Sep. 6, 2012

Related U.S. Application Data

(60) Provisional application No. 61/448,951, filed on Mar. 3, 2011.

(51) Int. Cl.
*H01S 3/14* (2006.01)

(52) U.S. Cl.
USPC .......................................................... 359/342

(58) Field of Classification Search
USPC ....................................... 359/342; 372/39, 66
See application file for complete search history.

(56) References Cited

U.S. PATENT DOCUMENTS

| | | | |
|---|---|---|---|
| 7,713,849 B2 * | 5/2010 | Habib et al. | 438/479 |
| 8,427,639 B2 * | 4/2013 | Moskovits et al. | 356/301 |
| 2008/0174775 A1 * | 7/2008 | Moskovits et al. | 356/301 |
| 2011/0166045 A1 * | 7/2011 | Dhawan et al. | 506/39 |
| 2012/0081703 A1 * | 4/2012 | Moskovits et al. | 356/301 |

OTHER PUBLICATIONS

Hirsch, L. R.; Jackson, J. B.; Lee, A.; Halas, N. J.; West, J., "A Whole Blood Immunoassay Using Gold Nanoshells", Analytical Chemistry 2003, 75, 2377-2381.
Rich, R. L.; Myszka, D. G., "Advances in surface plasmon resonance biosensor analysis", Current Opinion in Biotechnology 2000, 11, 54-61.
Bora, M.; Celebi, K.; Zuniga, J.; Watson, C.; Milaninia, K. M.; Baldo, M. A., "Near field detector for integrated surface plasmon resonance biosensor applications", Optics Express 2009, 17, 329-336.
Barnes, W. L.; Dereux, A.; Ebbesen, T. W., "Surface plasmon subwavelength optics", Nature 2003, 424, 824-830.
Ghaemi, H. F.; Thio, T.; Grupp, D. E.; Ebbesen, T. W.; Lezec, H. J., "Surface plasmons enhance optical transmission through subwavelength holes", Physical Review B 1998, 58, 6779-6782.
Lezec, H. J.; Degiron, A.; Devaux, E.; Linke, R. A.; Martin-Moreno, L.; Garcia-Vidal, F. J.; Ebbesen, T. W., "Beaming Light from a Subwavelength Aperture", Science 2002, 297, 820-822.

(Continued)

*Primary Examiner* — Mark Hellner
(74) *Attorney, Agent, or Firm* — Steinfl & Bruno, LLP

(57) ABSTRACT

Tunable plasmon resonant cavity arrays in paired parallel nanowire waveguides are presented. Resonances can be observed when the waveguide length is an odd multiple of quarter plasmon wavelengths, consistent with boundary conditions of node and antinode at the ends. Two nanowire waveguides can satisfy the dispersion relation of a planar metal-dielectric-metal waveguide of equivalent width equal to the square field average weighted gap. Confinement factors of over $10^3$ are possible due to plasmon focusing in the interwire space.

25 Claims, 22 Drawing Sheets

(56) References Cited

OTHER PUBLICATIONS

Morfa, A. J.; Rowlen, K. L.; Reilly, T. H.; Tenent, R.C.; van de Lagemaat, J., "Surface-plasmon enhanced transparent electrodes in organic photovoltaics", Applied Physics Letters 2008, 92, 243304-1-243304-3.

Tvingstedt, K.; Persson, N. K.; Inganas, O.; Rahachou, A.; Zozoulenko, I. V., "Surface plasmon increase absorption in polymer photovoltaic cells", Applied Physics Letters 2007, 91, 113514-1-113514-3.

Westphalen, M.; Kreibig, U.; Rostalski, J.; Luth, H.; Meissner, D., "Metal cluster enhanced organic solar cells", Solar Energy Materials and Solar Cells 2000, 61, 97-105.

Miyazaki, H. T.; Kurokawa, Y., "Controlled plasmon resonance in closed metal/insulator/metal nanocavities", Applied Physics Letters 2006, 89, 211126-1-211126-3.

Haynes, C. L.; Van Duyne, R. P., "Nanosphere Lithography: A Versatile Nanofabrication Tool for Studies of Size-Dependent Nanoparticle Optics", Journal of Physical Chemistry B 2001, 105, 5599-5611.

Haynes, C. L.; Van Duyne, R. P., "Plasmon-Sampled Surface-Enhanced Raman Excitation Spectroscopy", Journal of Physical Chemistry B 2003, 107, 7426-7433.

Michaels, A. M.; Nirmal, M.; Brus, L. E., "Surface-Enhanced Raman Spectroscopy of Individual Rhodamine 6G Molecules on Large Ag Nanocrystals", Journal of the American Chemical Society 1999, 121, 9932-9939.

Noginov, M.; Zhu, G.; Belgrave, A.; Bakker, R.; Shalaev, V.; Narimanov, E.; Stout, S.; Herz, E.; Suteewong, T.; Wiesner, U., "Demonstration of a spaser-based nanolaser", Nature 2009, 460, 1110-1113.

Zhang, S.; Berguiga, L.; Elezgaray, J.; Roland, T.; Faivre-Moskalenko, C.; Argoul, F., "Surface plasmon resonance characterization of thermally evaporated thin gold films", Surf. Sci. 2007, 601, 5445-5458.

Manjavacas, A.; de Abajo, F. J. G., "Robust Plasmon Waveguides in Strongly Interacting Nanowire Arrays", Nano Letters 2009, 9, 1285-1289.

Manjavacas, A.; de Abajo, F. J. G., "Coupling of gap plasmons in multi-wire waveguides", Optics Express 2009, 17, 19401-19413.

Stegeman, G. I.; Wallis, R. F.; Maradudin, A. A., "Excitation of surface polaritons by end-fire coupling", Optics Letters 1983, 8, 386-388.

Fernandez, A.; Nguyen, H. T.; Britten, J. A.; Boyd, R. D.; Perry, M. D.; Kania, D. R.; Hawryluk, A. M., "Use of interference lithography to pattern arrays of submicron resist structures for field emission flat panel displays", Journal of Vacuum Science & Technology B 1997, 15, 729-735.

Dionne, J. A.; Sweatlock, L. A.; Atwater, H. A.; Polman, A., "Plasmon slot waveguides: Towards chip-scale propagation with sub-wavelength scale localization", Physical Review B 2006, 73, 035407, 1-9.

Lezec, H. J.; Dionne, J. A.; Atwater, H. A., "Negative Refraction at Visible Frequencies", Science 2007, 316, 430-432.

Prodan, E.; Radloff, C.; Halas, N. J.; Nordlander, P., "A Hybridization Model for the Plasmon Response of Complex Nanostructures", Science 2003, 302, 419-422.

Sun, Z. J.; Zeng, D. Y., "Coupling of Surface Plasmon Waves in Metal/Dielectric Gap Waveguides and Single Interface Waveguides", Journal of the Optical Society of America B-Optical Physics 2007, 24, 2883-2887.

Johnson, P. B.; Christy, R. W., "Optical Constants of the Noble Metals", Physical Review B 1972, 6, 4370-4379.

* cited by examiner

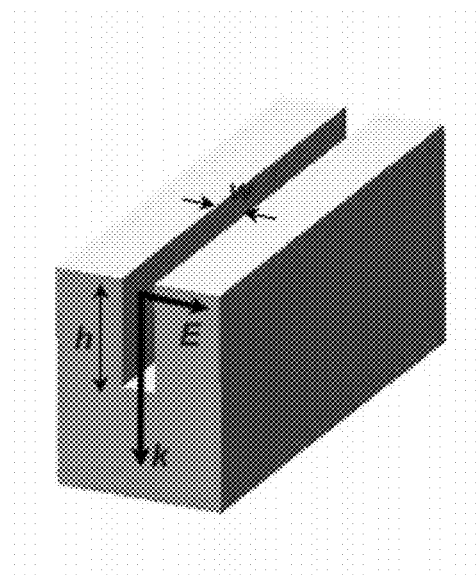
FIGURE 3A
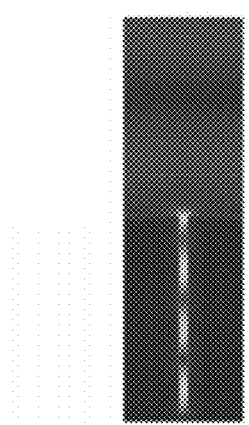 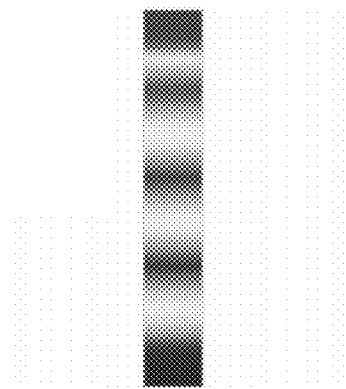 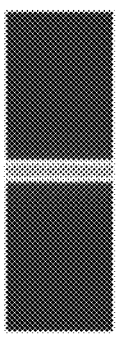
FIGURE 3B FIGURE 3C FIGURE 3D

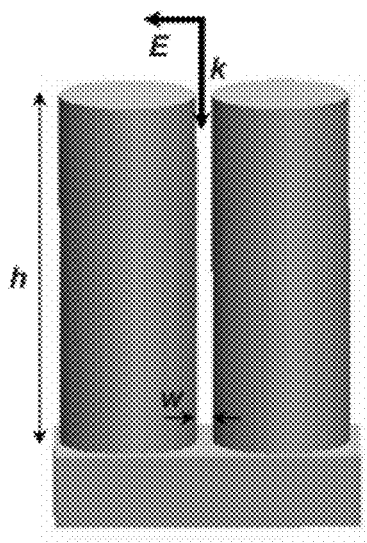
FIGURE 4A
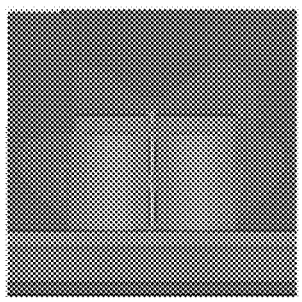 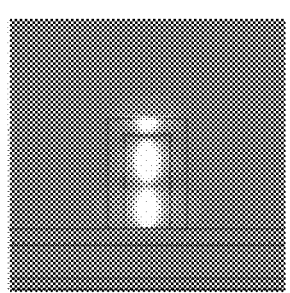 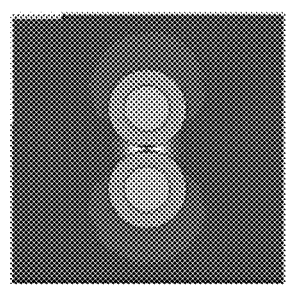
FIGURE 4B  FIGURE 4C  FIGURE 4D

PLASMON RESONANT CAVITIES IN VERTICAL NANOWIRE ARRAYS

STATEMENT OF GOVERNMENT GRANT

This invention was made with government support under Contract DE-AC52-07NA27344 awarded by the U.S. Department of Energy. The government has certain rights in the invention.

CROSS REFERENCE TO RELATED APPLICATIONS

The present application claims priority to U.S. Provisional Patent Application No. 61/448,951 for "Tunable Plasmon Resonant Cavities", filed on Mar. 3, 2011, the disclosure of which is incorporated herein by reference in its entirety.

TECHNICAL FIELD

The present disclosure relates to resonant cavities. More particularly, the present disclosure relates to plasmon resonant cavities in vertical nanowire arrays and related fabrication methods.

BACKGROUND

Surface plasmons, charge density waves propagating along metal-dielectric interfaces, are applied in bio-molecular detection (see references [1]-[3], incorporated by reference herein in their entirety), sub-wavelength optics (see references [4]-[6], incorporated by reference herein in their entirety), molecular specific surface enhanced Raman spectroscopy (SERS), plasmonic laser devices, and photovoltaic technology (see references [7]-[9], incorporated by reference herein in their entirety). These applications require high extinction strength of plasmonic resonances such that near field effects dominate physical behavior of the plasmonic resonances, hence design considerations for optimal structures aim to control both resonant wavelength and coupling with incident light.

Different geometries have been employed to study plasmonic structures. A horizontal layer approach provides excellent thickness control, but results in fewer plasmonic nanostructures per unit area (see reference [10], incorporated by reference herein in its entirety). Vertical structures provide good coverage, but require complex fabrication and are less amenable to large area substrates (see reference [11], incorporated by reference herein in its entirety).

SUMMARY

According to a first aspect, a plasmonic structure is presented, the structure comprising: a planar substrate; and an array of metal-coated dielectric nanowires end-connected substantially orthogonally to the planar substrate and in parallel arrangement with each other so that plasmon resonant gap-cavities capable of supporting propagation of gap plasmon modes are formed between adjacent pairs of said nanowires with one end of each of said plasmon resonant gap-cavities delimited by a surface of the planar substrate and another end of each of said plasmon resonant gap-cavities open ended.

According to a second aspect, a method of fabricating a plasmonic structure is presented, the method comprising: providing a planar dielectric substrate; producing an etch pattern on the planar dielectric substrate; etching the planar dielectric substrate based on the etch pattern to produce an array of dielectric nanowires end-connected substantially orthogonally to the planar dielectric substrate and in parallel arrangement with each other; and coating the dielectric nanowires with a metallic outer layer so that plasmon resonant gap-cavities capable of supporting propagation of gap plasmon modes are formed between adjacent pairs of said nanowires with one end of each of said plasmon resonant gap-cavities delimited by a surface of the planar substrate and another end of each of said plasmon resonant gap-cavities open ended.

BRIEF DESCRIPTION OF DRAWINGS

FIG. 3A shows a three dimensional model of the MDM infinite slot waveguide.

FIGS. 3B, 3C, and 3D show numerical simulation results of the electric field amplitude of the MDM infinite slot waveguide in the slot from the front, side and top, respectively.

FIG. 4A shows a two-nanowire plasmon resonant cavity, composed of two metallic cylinders separated by a small distance.

FIGS. 4B, 4C, and 4D show numerical simulation results of the electric field of the two-nanowire plasmon resonant cavity as viewed from the front, side and top, respectively.

DETAILED DESCRIPTION OF EXAMPLE EMBODIMENTS

As used herein, the terms "cavity", "nanocavity", "plasmon nanocavity", "plasmon resonant nanocavity", and "resonator" may be used interchangeably and can refer to a cavity in which plasmon standing waves may be excited.

As used herein, the term "aspect ratio" can refer to a ratio of height to diameter.

As used herein, the term "substantially orthogonally" can refer to a spatial relationship which may show a small, but not a significant, deviation from orthogonality.

As used herein, the term "vertical" can imply that a given item can be substantially orthogonal to a base, substrate, or other such similar item.

As used herein, the term "substantially hemispherical" can refer to a geometrical characteristic which may show a small, but not a significant, deviation from a state of being hemispherical.

As disclosed herein, structures which are described as being hemispherical may also be substantially hemispherical.

According to an example embodiment of the present disclosure, tunable plasmon resonant cavities in vertical wire arrays can be fabricated in a manner that combines the benefits of both the horizontal layer approach and vertical structures, providing high density and good control over the cavity size over a large area (4 inch wafer) uniform plasmonic substrate. Plasmon resonance in the 500-800 nm range can be tuned by controlling geometrical dimensions of the cavity. Future applications for nanocavities are envisioned in high sensitivity Raman spectroscopy (see references [12]-[13], incorporated by reference herein in their entirety) that requires high local electromagnetic fields and alignment between the plasmon resonance and excited and scattered light. Embodiments of the present disclosure can also be applied to Infrared (and other) Spectroscopy in that the concept shown for visible light can be extended to other wavelengths. Furthermore, embodiments of the present disclosure can also be applied to enhancing scintillation properties of other media that could be infiltrated (such as quantum dots).

A tunable nanocavity is of particular relevance for fabrication of plasmonic lasers which use surface plasmons instead of light to pump a lasing medium (see references [14]-[15], incorporated by reference herein in their entirety). Since device structure of the nanocavity relies on vertical free standing nanowires the tunable plasmon resonant cavity region can be filled with any material of choice. A plasmonic laser can comprise plasmon resonant cavities according to the present disclosure filled with an active gain medium. A plasmonic photovoltaic device can comprise plasmon resonant cavities according to the present disclosure filled with a photovoltaic material. In addition to high confinement factors shown, cavity plasmon resonance can be adjusted for maximum overlap with an absorbance of an active material.

Figure 1A:
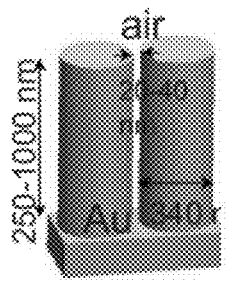
FIG. 1A shows a single plasmon resonant cavity based on a two-nanowire waveguide.

FIG. 1A shows a single plasmon resonant cavity based on a two-nanowire waveguide. A separation medium can be air of dielectric permittivity 1. Nanowire thickness can be approximately 340 nm, and height can range from 250 to 1000 nm. A wavevector of incident light can be oriented along the waveguide in transverse magnetic mode (magnetic field is parallel to substrate, perpendicular to a line joining centers of the two nanowires; magnetic field is perpendicular to electric field, which is parallel to a line joining centers of the two nanowires; both the electric field and the magnetic field are perpendicular to the wavevector of incident light). If the wavevector of incident light is not exactly aligned with the waveguide but rather forms a non-zero angle θ with an axis of the nanowires, then effective excitation of the waveguide decreases by a factor of 1/cos θ. Misalignment of the wavevector of incident light and the axis of the nanowires can occur either because the nanowires are not exactly orthogonal to a base or because incident light is provided at a non-zero incidence angle.

The single plasmon resonant cavity relies on a paired nanowire waveguide that can support propagation of gap plasmon modes (see references [16]-[17], incorporated by reference herein in their entirety) when a separation between the two nanowires is less than 50 nm. The single plasmon resonant cavity can be delimited by a reflective metallic mirror at one end and an open end on an opposite end for a more effective incident light-plasmon coupling (see reference [18], incorporated by reference herein in its entirety). Resonances can occur when a cavity length is an odd multiple of quarter plasmon wavelengths due to boundary conditions of node at the minor and anti-node at the open end.

Figure 1B:
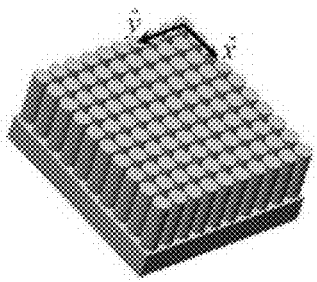
FIG. 1B shows a rectangular array of cavities, of a type shown in FIG. 1A, on a planar substrate.

FIG. 1B shows a rectangular array of cavities, of a type shown in FIG. 1A, on a planar substrate. Arrows indicate lattice vectors of the rectangular array.

Figure 1C:
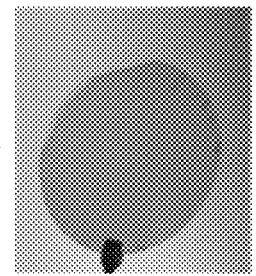
FIG. 1C shows a large area fabrication of plasmon nanocavities on a four-inch diameter substrate.

FIG. 1C shows a large area fabrication of plasmon nano-cavities on a four-inch diameter substrate.

Figure 1D:
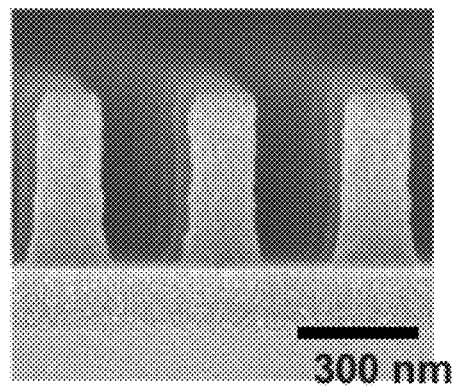
FIG. 1D shows a side view of photoresist nanowires fabricated by laser interference lithography.

FIG. 1D shows a side view of photoresist nanowires fabricated by laser interference lithography.

Figure 1E:
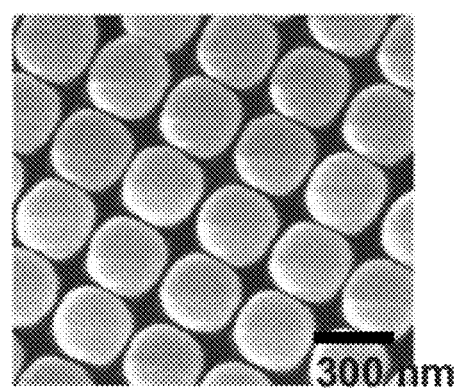
FIG. 1E shows a top view of a metallic nanowire cavity array coated with gold. A wire center-to-center distance is 360 nm and an edge to edge gap is 35 nm.

FIG. 1E shows a top view of a metallic nanowire cavity array coated with gold. A wire center-to-center distance can be 360 nm and an edge to edge gap can be 35 nm.

A two dimensional rectangular array of vertical resonant cavities can be fabricated on a planar substrate as shown in FIGS. 1B-1E. Each nanowire can be surrounded by four closest neighbors corresponding to two resonant cavities per nanowire, for a density of $3.85 \cdot 10^8$ cavities/cm$^2$. Vertical wire geometry can enable large area fabrication (as shown in FIG. 1C) and far field optical characterization. No inter-coupling between cavities is expected in these structures, since the size of the nanowires can be an order of magnitude larger than a penetration depth of the electric field in a metal coating of the nanowires.

Photoresist wire arrays can be patterned on a fused silica substrate using laser interference lithography under conditions described previously (see reference [19], incorporated by reference herein in its entirety). The pattern can be transferred onto the fused silica substrate by reactive ion etching, etching away portions of the substrate which are not covered by the photoresist wire arrays, thus creating silica nanowire arrays. Silica nanowires can be coated with alumina by atomic layer deposition so that inter-wires gap is approximately 75 nm. Since alumina deposition is self-limiting, thickness of the alumina can be increased in conformal single molecule layer steps. Finally, a 20-40 nm thick coating (e.g., gold coating) can be deposited by sputtering until an edge to edge distance between adjacent wires approaches 20-40 nm. Gold can be preferable in some applications, such as spectroscopy, since it is chemically inert. Alumina deposition is very conformal, and provides uniform coverage while gold tends to deposit more heavily on top of the structure. Thus alumina deposition can be performed prior to gold deposition. Gold or any other metal can also be sputtered directly onto the substrate without prior alumina deposition.

Figure 2A:
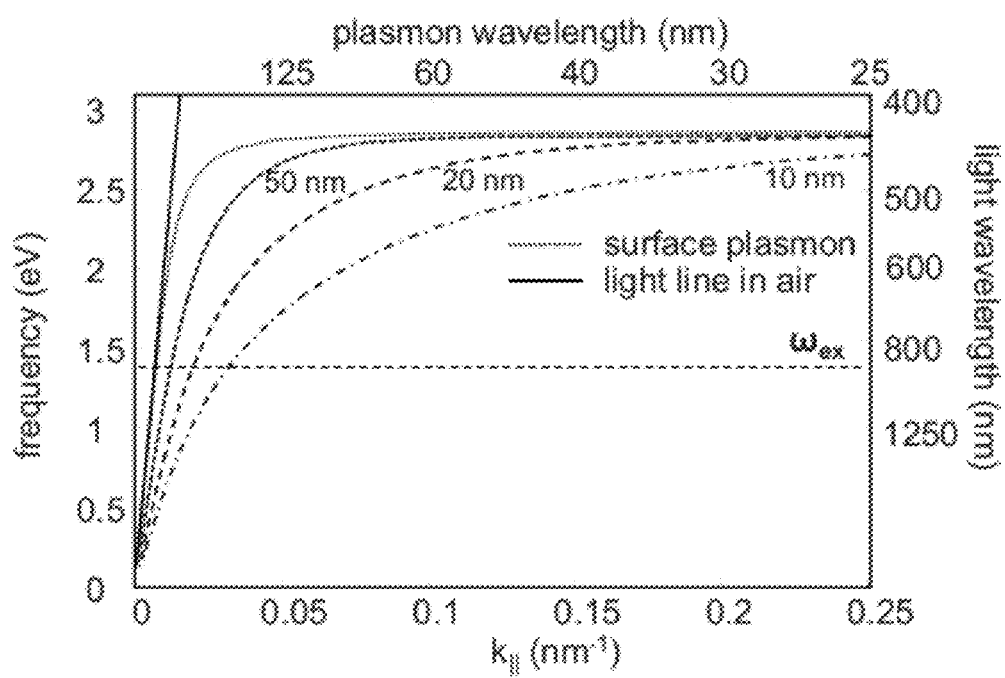
FIG. 2A shows dispersion relations for a gold-air-gold or metal dielectric metal (MDM) symmetric plasmon for different air thicknesses.

FIG. 2A shows dispersion relations for a gold-air-gold or metal dielectric metal (MDM) symmetric plasmon for different air thicknesses. Numbers near the curves indicate width of the dielectric (air). For incident light along the waveguide of radian frequency $\omega_{ex}$, plasmon modes of the same frequency and wavevector given by a dispersion curve are excited.

Figure 2B:
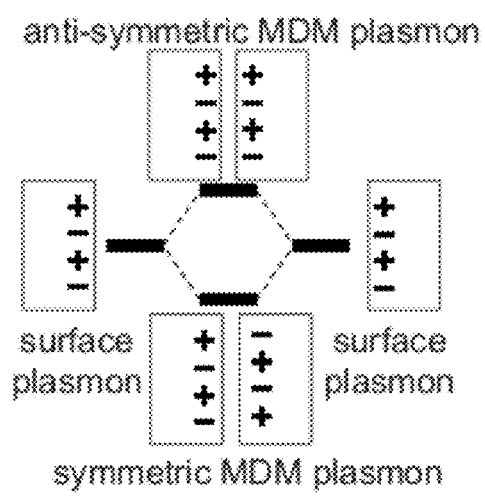
FIG. 2B shows qualitative behavior of the MDM plasmon based on a hybridization model.

FIG. 2B shows qualitative behavior of the MDM plasmon based on a hybridization model. When two elementary thin film plasmons are brought in close proximity two new states are formed: a symmetric (low energy) and antisymmetric (high energy state).

Figure 2C:
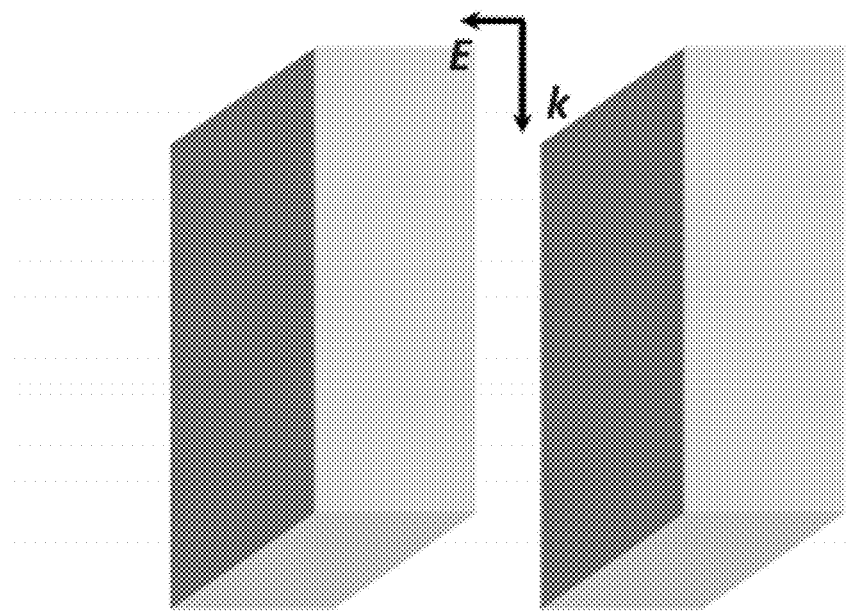
FIG. 2C shows a schematic representing an MDM waveguide.

FIG. 2C shows a schematic representing an MDM waveguide. The plasmon modes are excited by light propagating with wavevector k, along the planar waveguide with the electric field vector E, perpendicular to the metal surface.

The two nanowire plasmon waveguide (shown in FIG. 1A) properties can be explained using an underlying planar metal-dielectric-metal (MDM) waveguide that is composed of two semi-infinite metal volumes separated by a dielectric of finite thickness (shown in FIG. 2C). The planar MDM waveguide is sufficiently simple to allow an analytical calculation of a dispersion curve based on geometry and dielectric properties of materials of which the waveguide is constructed. The two nanowire waveguide can be approximated as an MDM waveguide of effective width $w_{\textit{eff}}$ that can be calculated using an appropriate gap weighting metric; this is effectively a technique of decomposing the two nanowire waveguide into a continuum of elementary planar waveguides. For example, for an optical extinction coefficient, the effective width can be equal to the gap weighted with a square average of a field strength. The technique of decomposing the two nanowire waveguide into a continuum of elementary planar waveguides can be extended to other geometries providing a straightforward way to calculate the dispersion relation of arbitrary shape waveguides (e.g. wedges, grooves).

Dispersion relations for MDM plasmons can be determined by solving for propagating modes along the waveguide under continuity conditions at metal dielectric boundaries while satisfying Maxwell's equations (see references [20]-[21], incorporated by reference herein in their entirety). MDM solutions can degenerate into symmetric and anti-symmetric modes, defined by a parity of an electric field in a direction perpendicular to the dielectric sheet, with respect to a mid-plane. Single interface surface plasmon modes can be recovered when separation between two metal portions of the MDM waveguide is increased beyond an evanescent decay length, where evanescent decay length refers to a distance past which field intensity drops by a factor of 1/e.

The plasmon degeneracy can be understood in the plasmon hybridization model (see reference [22], incorporated by reference herein in its entirety), shown in FIG. 2B, in which the MDM plasmon can be decomposed into two interacting single metal interface plasmons. This situation is analogous to the formation of chemical bonds where valence orbitals can interact to form a bond. In such an analogy, each individual single metal interface plasmon can correspond to a valence orbital. Electric field of a single metal interface plasmon can be plotted as a function of position in a manner similar to a valence orbital representing a function of electron probability distribution in space. A low energy or "bonding" state corresponds to a symmetric mode and a high energy or "anti-bonding" state to an anti-symmetric mode. A symmetric or "bonding" MDM plasmon can be excited by incident light.

Coupling efficiency between light (electromagnetic plane wave) and MDM plasmons is proportional to spatial and temporal overlap of the modes (see reference [23], incorporated by reference herein in its entirety). Spatial overlap refers to the light and the MDM plasmon having a similar spatial field distribution, and temporal overlap refers to the light and the MDM plasmon having a same frequency. Coupling efficiency can be calculated according to the following equation:

$$\eta = \frac{\langle H_{plasmon} \mid H_{photon} \rangle^2}{|H_{plasmon}|^2 \cdot |H_{photon}|^2} \quad (1)$$

where $\eta$ represents the coupling efficiency and $H_{plasmon}$ and $H_{photon}$ represent field profiles for the plasmon and electromagnetic plane wave excitation modes. The expression in the numerator represents a dot product of field profiles corresponding to the plasmon and the electromagnetic plane wave. The more closely the field profiles corresponding to the plasmon and the electromagnetic plane wave match, the easier it can be to transfer energy from the light to the plasmon. Electric field of incident light is constant across the gap (symmetric) if the dielectric width is much smaller than the light wavelength; hence, the coupling efficiency can be non-zero for the symmetric mode.

The dispersion relation for the symmetric mode can be given by the equation:

$$\tanh\left(ik_\perp^d \frac{w}{2}\right) = -\frac{\varepsilon_d k_\perp^m}{\varepsilon_m k_\perp^d} \quad (2)$$

where $k_\perp^d$ and $k_\perp^m$ represent perpendicular (perpendicular to a plane of interface between the dielectric and metal) components of the plasmon wavevector in the dielectric and metal, $\varepsilon_d$ and $\varepsilon_m$ represent relative permittivities for the dielectric and metal, respectively, and w represents width of dielectric sheet. In FIG. 2A, the dispersion relations for gold-air-gold waveguides of different air thicknesses are plotted. A dielectric function of gold is based on a Drude model fit for published optical constants of gold (see reference [24], incorporated by reference herein in its entirety).

FIG. 3A shows a three dimensional model of the MDM infinite slot waveguide. The plasmon modes are excited by transverse magnetic polarized light of normal incidence to a metallic plane. Dark arrows indicate the orientation of the wavevector and electric field of the excitation light.

Two different cavity types can be analyzed. The first cavity type which can be analyzed, the MDM slot waveguide, can be a rectangular groove of height h and width w and infinite length indented in a semi-infinite metallic volume as shown in FIG. 3A. This ideal structure can allow direct comparison with the exact analytical dispersion relation calculated above for the MDM waveguide.

FIG. 4A shows a two-nanowire plasmon resonant cavity, composed of two metallic cylinders separated by a small distance. An incident light electric field is oriented normal to the side surface of the wires (transverse magnetic mode). The two-nanowire plasmon resonant cavity shown in FIG. 4A is the second cavity types which can be analyzed. The plasmonic features of a vertical wire nanocavity can be similar to those of the MDM slot waveguide, both can show resonances when the length of the cavity is an odd multiple of quarter plasmon wavelengths. Furthermore, the two nanowire waveguide can satisfy the dispersion relation of a modified planar MDM waveguide.

The two cavities can each be modeled as a waveguide of finite length, delimited by a metallic interface at the bottom and dielectric on top. Plasmon MDM type modes can be excited by light normally incident on an open end side of the cavity. A photon field can overlap with the plasmon cavity over a thin region with a thickness comparable to the skin depth of gold. Free electrons in the metal can oscillate with the excitation light frequency $\omega_{ex}$ and plasmon waves with wavevector given by the dispersion relation calculated in Equation 2 can propagate along the waveguide. On a closed metallic end, a reflection with a $\pi$ phase shift can occur and a plasmonic standing wave can form along the waveguide.

Structural resonant features can be derived from boundary conditions at the metal minor (node) and open dielectric side (anti-node):

$$kh = \pi\left(m + \frac{1}{2}\right) \quad (3)$$

where k represents a plasmon wavevector along the inter-wire region, h represents a wire height, and m=0, 1, 2 . . . represents a resonance order. Plasmon states for which the wavevector satisfies the resonance condition in Equation 3 can couple more strongly with the incident light and can have a higher extinction coefficient (absorptivity), resulting in minima in the reflection spectrum.

Figure 3E:
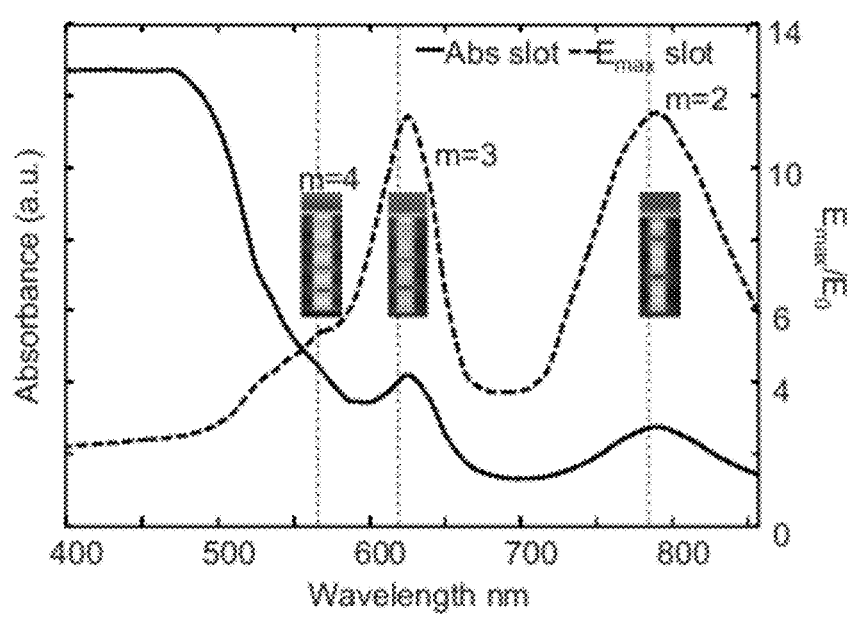
FIG. 3E shows maximum electric field amplitude in the cavity of the MDM infinite slot waveguide normalized to the incident light field and optical absorbance of the slot as a function of wavelength.

FIGS. 3B, 3C, and 3D show numerical simulation (conducted using finite elements analysis) results of the electric field amplitude of the MDM infinite slot waveguide in the slot from the front, side, and top, respectively. FIG. 3E shows maximum electric field amplitude in the cavity of the MDM infinite slot waveguide normalized to the incident light field and optical absorbance of the slot as a function of wavelength. Resonances of order 2, 3, and 4 can be observed at 800, 650, and 565 nm in both absorbance and electric field plots. Below 600 nm material absorbance of gold dominates optical properties of the resonator. Dashed vertical lines indicate positions of resonance as calculated from Equation 2. A small discrepancy with the numerical simulation can be attributed to a phase change at the ends of the cavity.

The cavity orders are illustrated by insets representing the electric field amplitude for each resonance. Although resonance for a case of m=4 may not display maximal value for either maximum electric field amplitude or optical absorbance of the slot, maximum electric field amplitude normalized to the incident light field and optical absorbance of the slot exhibit shoulders, indicating resonance. Also, the inset representing the electric field amplitude for the case of m=4 indicates resonance.

Numerical simulations were carried out for MDM slot waveguides of height 500 nm and width 20 nm under excitation light normally incident on a substrate surface of the MDM slot waveguide in the transverse magnetic mode. Resonant modes can be observed in plots of the electric field amplitude when standing plasmonic waves are formed, as shown in FIG. 3C. Peaks can be observed for resonances of order m=2 (785 nm), m=3 (620 nm) and m=4 (565 nm). Wavelength dependence of substrate absorbance, calculated as heat dissipation in metallic material of the MDM slot waveguide, and the electric field amplitude show peaks at the same location. This finding allows correlation of the near-field properties (e.g. field profile of the plasmonic structure) of the plasmonic cavity using far field characterization techniques such as reflectance and transmission. An electric-field profile of the modes in a single cavity can correlate well with simulations performed for larger nanowire arrays (data not shown), due to strong confinement of the modes in the inter-wire space that can minimize the interaction between neighboring resonators.

Figure 4E:
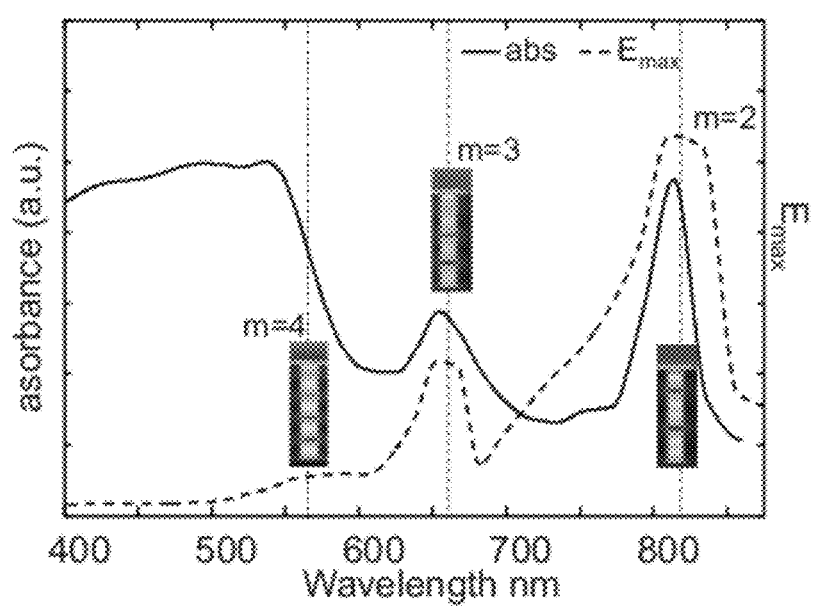
FIG. 4E shows maximum electric field amplitude in the two-nanowire plasmon resonant cavity normalized to the incident light field and optical absorbance of the slot as a function of wavelength.

FIGS. 4B, 4C, and 4D show numerical simulation results of the electric field of the two-nanowire plasmon resonant cavity as viewed from the front, side and top, respectively. FIG. 4E shows maximum electric field amplitude in the two-nanowire plasmon resonant cavity normalized to the incident light field and optical absorbance of the slot as a function of wavelength. Resonances of order 2, 3, and 4 can be observed at 800, 650 and 565 nm.

A three-dimensional simulation (as shown in FIG. 4) of the two nanowire cavity can be compared with the MDM slot model. Similar characteristics can be observed for the electric field profile, and absorbance spectrum. As in the simulations of the MDM slot model, the plasmon modes can be excited by transverse magnetic normal incident light. Resonances can be observed when the height of the wire is an odd multiple of quarter plasmon wavelengths. The plasmon modes can be strongly confined to an inter-wire space where the amplitude of the electric field can be two orders of magnitude larger than in the rest of the structure.

Figure 5A:
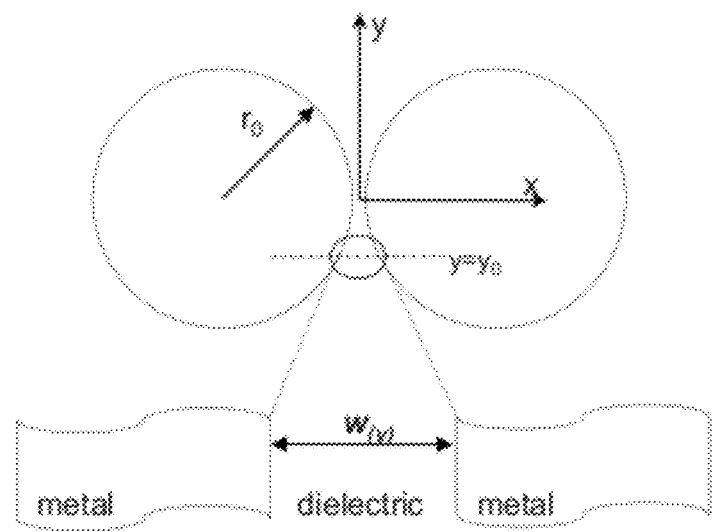
FIG. 5A shows an equivalence between the two nanowire waveguide and the MDM slot waveguide.

FIG. 5A shows an equivalence between the two nanowire waveguide and the MDM slot waveguide. At the top of FIG.

5A is a top view of the two nanowires. The wire waveguide can be approximated for each point along the circumference with a planar MDM waveguide. An effective width can be calculated by averaging the variable width over the square of the field in the gap. Such calculation can be performed using either magnetic field or electric field. Using magnetic field (H) allows for simpler analytical form although simulations normally use electric field (E). However, either type of field may be derived from the other using Maxwell's equations.

Figure 5B:
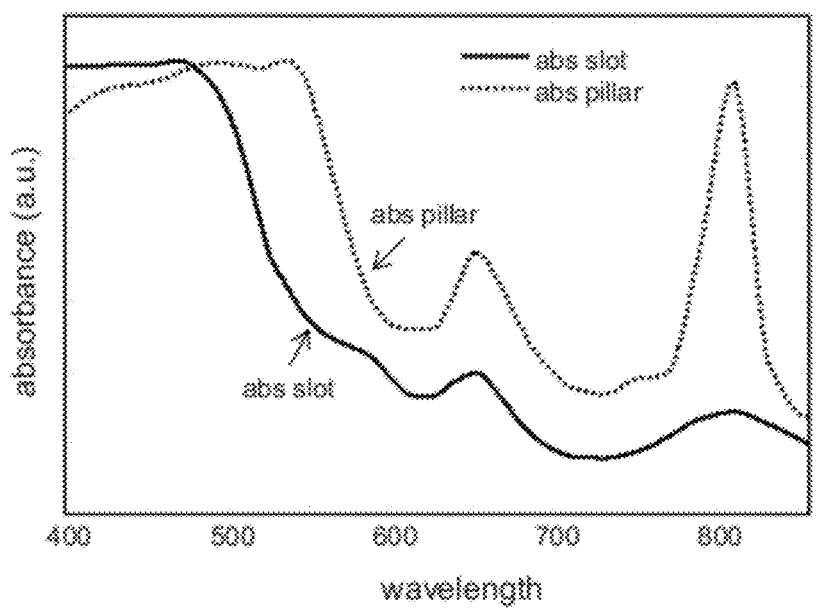
FIG. 5B shows a comparison of absorbance spectra and electric field maximum amplitude between nanowires (dotted line) and slot (solid line) cavities having the same effective width.

FIG. 5B shows a comparison of absorbance spectra and electric field maximum amplitude between nanowires (dotted line) and slot (solid line) cavities having the same effective width.

Figure 5C:
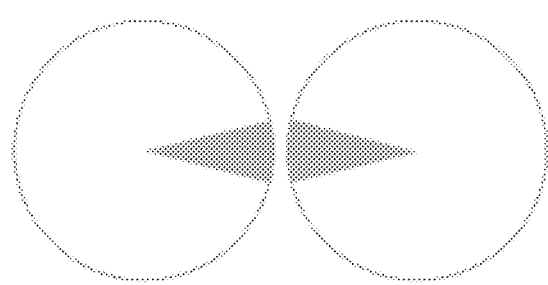
FIG. 5C shows a circular sector with a ±12 degrees opening (shaded region).

The MDM slot model can predict the optical properties of the two nanowire cavity when the equivalent spacing is taken into account as shown in FIG. 5B. The effective distance between the wires can be calculated using coupling mode theory (Equation 1). Assuming that both photon and plasmon magnetic fields are normalized to unity and that the photon field is nearly constant across the gap, a coupling efficiency at each point along the y axis, as shown in FIG. 5A, can be given by:

$$\eta_{(y_0)} \propto \left( \int_{y=y_0}^{} H_{plasmon}^{y} dx dz \right)^2 \quad (4)$$

where $H_{plasmon}^{y}$ represents a y component of the plasmon magnetic field (x and z components are null). The coupling efficiency between photons and plasmons can therefore be proportional to the square of the field average. Based on coupling mode theory argument presented above, an effective separation of two adjacent nanowires can be calculated as an average width weighted by the gap weighting metric described earlier. This key finding allows derivation of the dispersion relation of complex plasmonic waveguides using a much simpler planar waveguide. Although the cylindrical geometry outside the inter-wire region deviates from the parallel interface model, 90% of total electromagnetic field energy can be concentrated in a circular sector with a ±12 degrees opening. FIG. 5C shows a circular sector with a ±12 degrees opening (shaded region). For specified dimensions of the fabricated array (wire center-to-center distance of 360 nm), the effective width can be approximately two times an edge to edge wire distance (15-35 nm). In FIG. 5B the extinction spectrum for the slot cavity in FIG. 3C is compared with the extinction spectrum of the nanowire cavity in FIG. 4C. Wire cavities that resonate at the same frequency as the slot cavities show a higher maximum electric field and extinction coefficient. This can be explained by an increase in surface charge density which can be inversely proportional to a radius of curvature of the wire.

Although the plasmon cavity modes are excited by light polarized in the transverse magnetic mode (e.g. the electric field vector is oriented along the wire center to center direction) the wire array optical properties can be independent of polarization. The substrate contains two sets of plasmonic cavities aligned along the two perpendicular lattice vectors, as shown in FIG. 1B. The TM mode of the incident light as referenced to the first subset ($\hat{x}$), corresponds to the TE mode for the second one ($\hat{y}$), and orthogonal decomposition of the incident electric field with respect to the two axes explains polarization invariance.

It can be useful to compare the mode profile of the MDM slot shown in FIG. 3B with the same order mode for the wire cavity shown in FIG. 4B. Although the front, top and side views of the MDM slot are redundant, they are included for a more clear comparison with the wire cavity mode. Plasmons of the two-nanowire waveguide can be confined in both lateral dimensions. Along the direction normal to the wire surface the confinement can be determined by charge screening of the electric field in the metal layer. The two-nanowire waveguide can be viewed as similar to a capacitor where opposite charges reside on opposing conductor surfaces. Confinement in the second lateral direction can result from formation of a plasmon energy trap. As a distance between opposing conductor surfaces decreases, potential energy decreases, resulting in more force such that energy can be trapped within the waveguide because more energy is needed to escape from a location of close separation between conductors. Opposite polarity surface charges of the symmetric mode can minimize the dipole interaction energy when the distance is shortest. Since effective MDM waveguide separation can be increasing rapidly away from the inter-wire region, a strong energy gradient can focus the plasmons in the inter-wire space. The plasmon energy trap can be understood from the dispersion relations in FIG. 2A; energy of the MDM plasmon modes is always lower than the energy of single metal-dielectric interface for the same propagating wavevector k. This self-confinement feature can make the two wire plasmonic waveguides ideal candidates for high density plasmonic interconnects since the packaging density can be increased significantly. Three dimensional sub-wavelength confinement, where energy can be trapped in a space much smaller than the wavelength of incident light, becomes possible if the cavity length is smaller than the wavelength of the excitation light. For 250 nm tall cavities a confinement factor can be estimated to be approximately 1800, where confinement factor can be estimated as a ratio between a dielectric core volume containing 90% of the electromagnetic energy density and a cube of the excitation wavelength.

Figure 6:
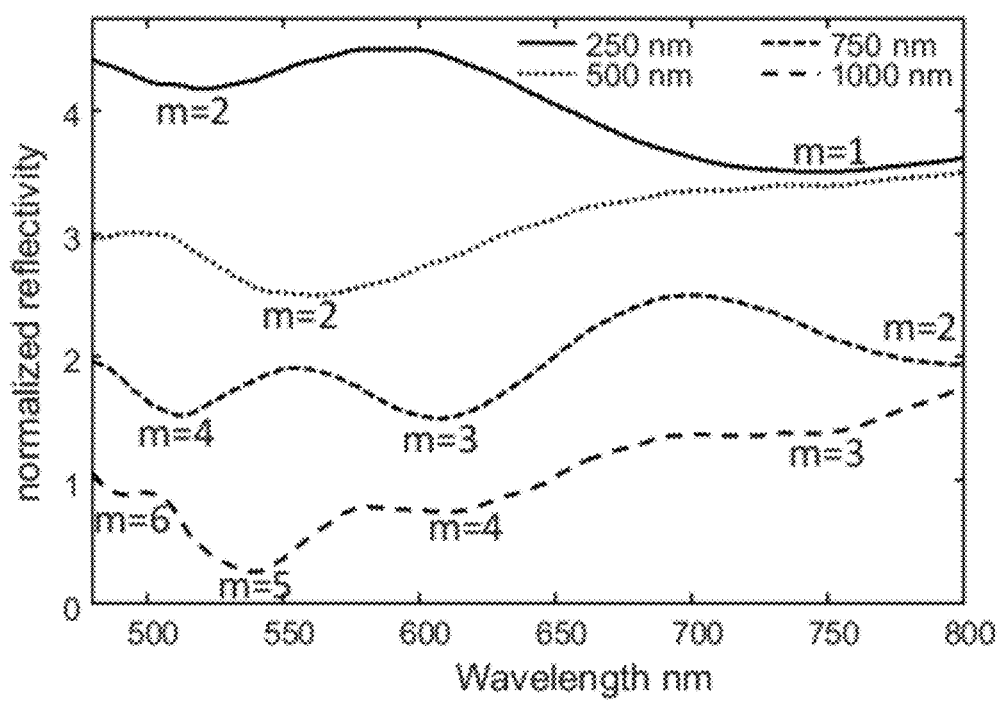
FIG. 6 shows normalized reflectivity plots for nanowire cavity arrays of height 250, 500, 750 and 1000 nm.

FIG. 6 shows normalized reflectivity plots for nanowire cavity arrays of height 250, 500, 750 and 1000 nm. Incident light is non-polarized and perpendicular to the substrate. Reflectivity minima can correspond to nanocavity excitation of plasmon resonances labeled by their order m.

The nanowire cavity array substrates (e.g., the structure comprising both the nanowires and the metallic mirror surface upon which they are anchored) were optically characterized by measuring wavelength dependent normal incidence reflectivity with a NanoSpec 3000 tabletop film analysis system (Nanometrics Inc., Milpitas, Calif.). Reflectivity plots were normalized to a 100 nm thick gold film to account for material specific absorbance as shown in FIG. 6. Excitation of plasmons within the cavity can increase the extinction coefficient of the substrate and resonances can be observed as minima in the reflectivity data. The cavity order can be identified using numerical simulations and the analytical expression of the dispersion curve.

Optical diffraction patterns (seen in FIG. 1C) can be observed on the array samples at high incidence angles and for short wavelengths. Dark-field measurements can identify a first order diffraction peak at 425 nm for a 70° angle between incident and diffracted beams (data not shown). The term "dark-field measurements" can refer to a measurement technique where incident light can be provided at a high incidence angle (e.g. 70°) and diffracted light outbound at a normal angle can be measured. Decreasing an angle between the two beams shifts the diffraction peak toward shorter wavelengths such that no interference effects are expected in the spectrum collected at normal incidence.

A plasmon resonance condition can be changed by modifying either a wire height or a wire separation. Modifying the wire height can alter the cavity length, while modifying the wire separation can change the plasmon propagating wavevector according to the dispersion relation. For a vertical wire cavity of given height and separation, resonances of monotonically decreasing order can be observed with increasing excitation wavelength and the highest order resonances can be located towards the blue side of the spectrum.

Figure 7A:
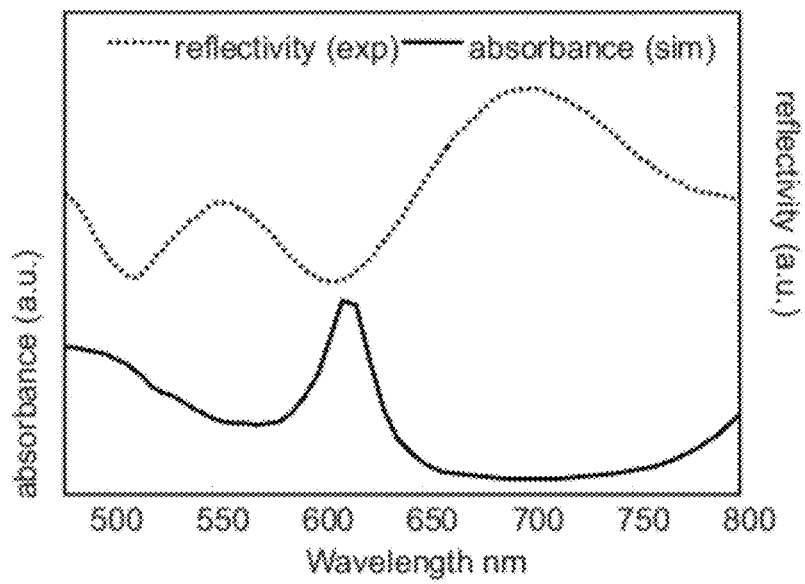
FIG. 7A shows measured reflectivity and simulated absorbance in the nanowire array.
Figure 7B:
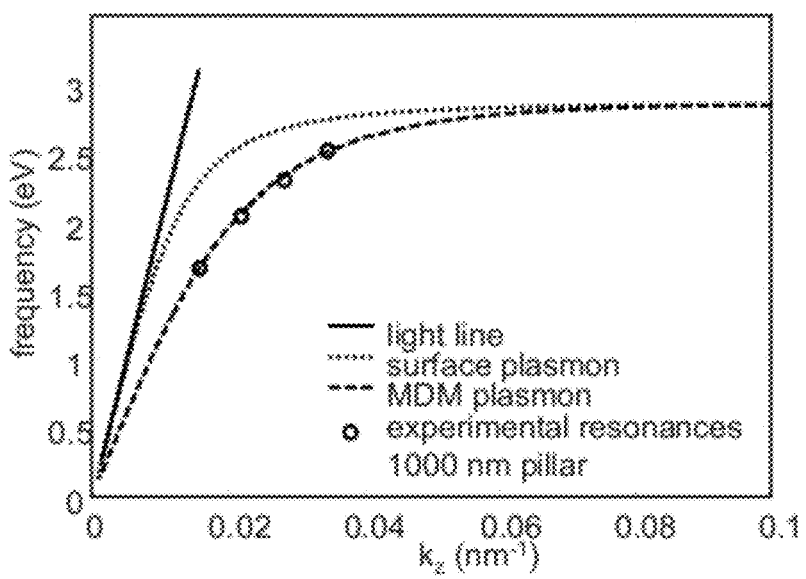
FIG. 7B shows analytical and experimental dispersion relations.

FIG. 7A shows measured reflectivity and simulated absorbance in the nanowire array. Minima of the experimental reflectivity align with the simulated absorbance maxima. FIG. 7B shows analytical and experimental dispersion relations. The dashed curve shows analytical calculation based on MDM infinite waveguide using an effective gap separation. Circles represent experimental points calculated from 1000 nm tall wire reflectivity measurements. Frequency is denoted using units of eV (electron volts, a measure of energy) for ease of discussion. Energy and frequency are related by a multiplication relationship with Planck's constant as a factor being multiplied by frequency to yield energy.

Numerical simulations of the far and near field patterns show good agreement with the experimental data. Measured reflectivity was compared with numerical simulations of the absorbance as shown in FIG. 7A. Resonances can be observed as minima in the measured reflectivity and as maxima in the simulated absorbance. Typically experimental data has a lower resonance quality factor than numerical simulations, probably because of additional roughness effects. Below 550 nm there is a discrepancy between simulation and experiment. It is possible that in this spectral range optical properties of the 20-40 nm gold coating differ from bulk values used in modeling of the nanowire array used to produce the simulation.

Plasmon wavelength can be calculated from Equation 3, knowing the cavity length and cavity order. The resonances measured in the experimental reflectivity can be compared with numerical simulations to determine the resonance order and to calculate the plasmon wavevector. Further, the wavevector and frequency points can be plotted along the dispersion curve for the MDM waveguide (as shown in FIG. 7B) from the analytical expression in Equation 2, using a separation value that best fit the data. Good agreement between analytical calculation of dispersion relation, numerical simulation of electric field and absorbance, and experimental data reflectivity show that the two-nanowire plasmon nanocavity can be approximated using a variable width MDM waveguide. The nanowire geometry allows for a stronger confinement resulting in higher fields and quality factors.

Nanowires with Hemispherical Caps

In another example embodiment a plasmonic structure tunable from ultra-violet to infrared wavelengths with maximum absorbance strength over 95% at resonance due to a highly efficient coupling with incident light is presented. Compared with the previous embodiments, alumina deposition can result in flatter wire structures while metal deposition can result in wire structures with rounder tops. A slight change in resonance can be observed when comparing flat tops and round tops. Additional fundamental mode overtones can be excited at higher frequencies extending the absorbance range to multiple wavelengths. The concept of a black plasmon resonator for which the overtones can be spaced arbitrarily close such that incident radiation can be absorbed with high efficiency over the entire visible range is presented. Limitations for implementing such structures are discussed and it can be shown that for gold, silver or aluminum plasmon resonator arrays, visible averaged absorbance (400 to 800 nm) can be increased above 75%, a remarkable feature considering that all three metals can be used to fabricate highly reflective optical mirrors. The significance of aluminum nanostructures for large scale applications is underscored by the fact that it is the least expensive pure metal and the third most abundant element in the Earth's crust after oxygen and silicon. Silver exhibits the lowest amount of loss, while gold is chemically inert.

Figure 8A:
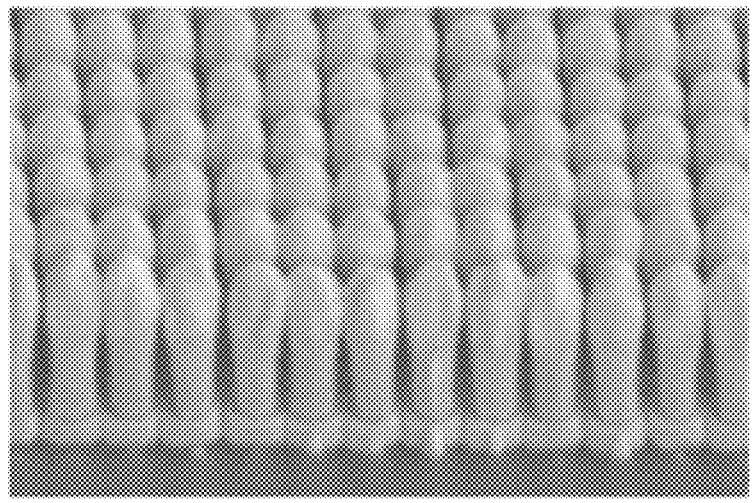
FIG. 8A shows a scanning electron micrograph of a 360 nm period rectangular array of variable height vertical nanowires viewed from the side.
Figure 8B:
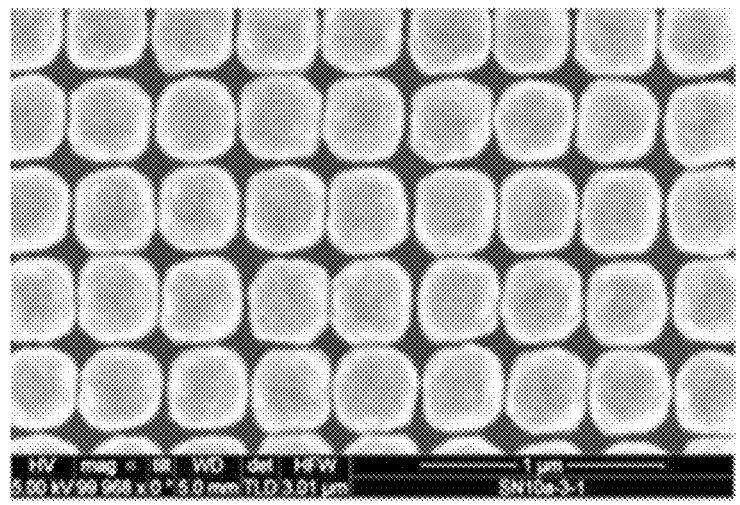
FIG. 8B shows a scanning electron micrograph of a 360 nm period rectangular array of variable height vertical nanowires viewed from the top.

FIG. 8A shows a scanning electron micrograph of a 360 nm period rectangular array of variable height vertical nanowires viewed from the side. FIG. 8B shows a scanning electron micrograph of the 360 nm period rectangular array of variable height vertical nanowires viewed from the top.

Figure 8C:
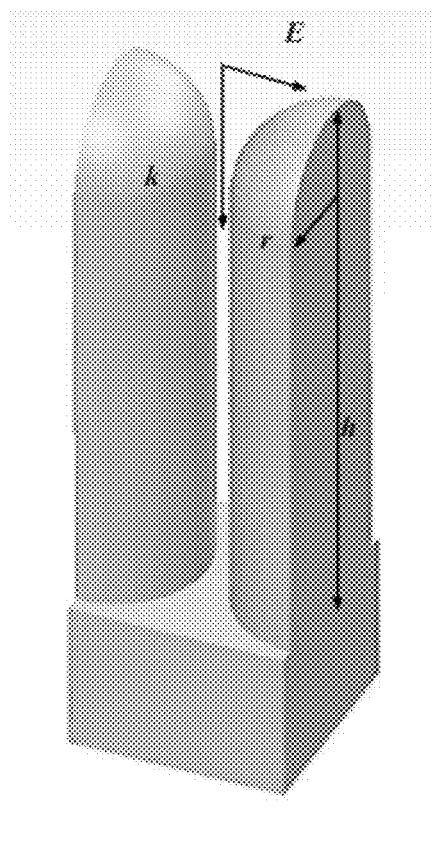
FIG. 8C shows a unit cell of a rectangular array centered on a plasmon nanocavity.

FIG. 8C shows a unit cell of a rectangular array centered on a plasmon nanocavity. The geometry of a rectangular array of variable height vertical nanowires can be specified by pitch, and radius and height of the array. The plasmon nanocavity can be optically excited with normal incidence light polarized in the transverse magnetic mode A plasmon substrate in this embodiment can be the 360 nm period rectangular array of variable height vertical nanowires coated with gold, silver or aluminum as shown in FIG. 8. Plasmon modes can be excited in a metal-dielectric-metal waveguide composed of two parallel nanowires that can be separated closer than 100 nm from edge to edge as shown in FIG. 8C. A smaller separation distance between nanowires can result in stronger coupling between the incident light and plasmons. Therefore, a separation of 50 nm or less between nanowires can result in even stronger coupling. An optical cavity can be delimited by a metallic minor at bottom and a curved tapered opening at top. Standing wave modes formed by the interference of forward and backward propagating waves can be determined by the dispersion relation of the waveguide and the phase shifts at each end:

$$2k_{sp}h+\phi_1+\phi_2=2m\pi,$$

where $k_{sp}$ represents the wavevector of the surface plasmon wave, h represents the length of the cavity, $\phi_1$ and $\phi_2$, represent phase changes at the top and bottom boundaries and m represents the resonance order. This equation can reduce to equation (3) when the top boundary (open end) is considered a node and the bottom boundary (metallic mirror) is considered an anti-node.

Figure 8D:
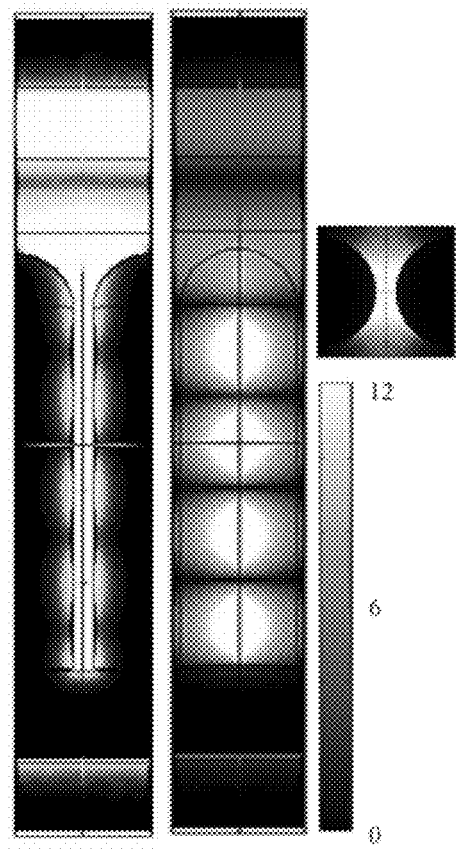
FIG. 8D shows simulations of the electrical field amplitude in the plasmon nanocavity seen from front, side and top.
Figure 8E:
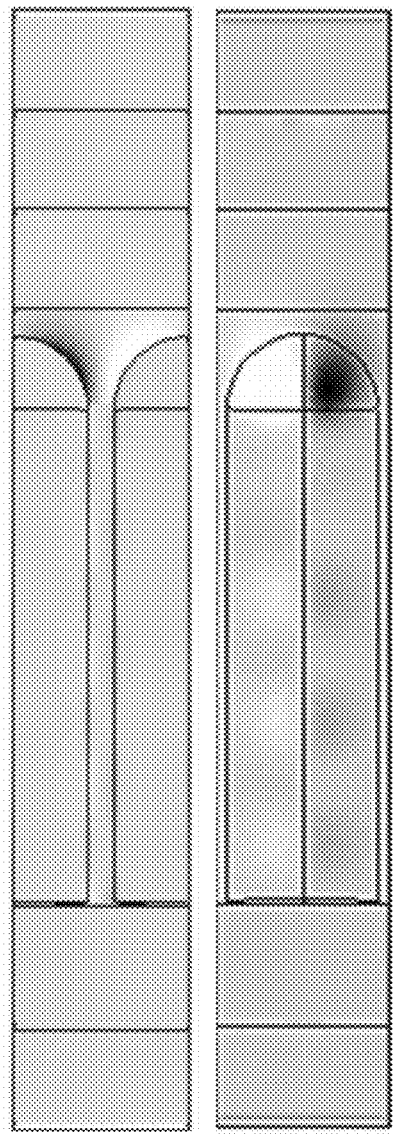
FIG. 8E shows nanofocusing of electromagnetic energy in the cavity mode and power flow in vertical symmetry planes of the cavity.

FIG. 8D shows simulations of the electrical field amplitude in the plasmon nanocavity seen from front, side and top. FIG. 8E shows nanofocusing of electromagnetic energy in the resonant mode and power flow in vertical symmetry planes of the cavity. Spherical ending of the nanowire enables efficient coupling between incident light and the plasmon modes.

Figure 9A:
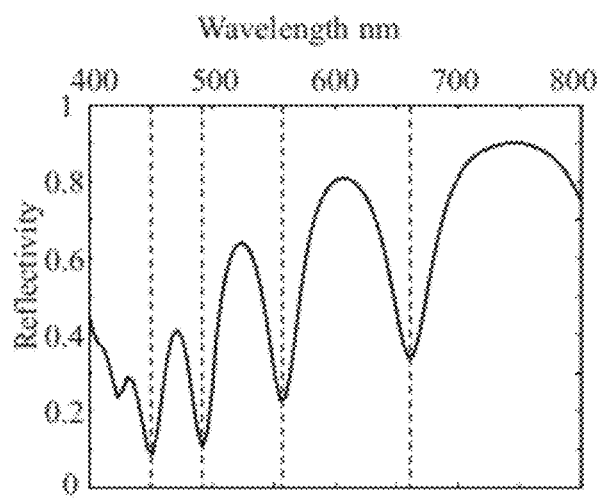
FIG. 9A shows normal incidence reflectance (in an example experiment) for a silver nanocavity 1000 nm long, 60 nm wide, showing resonances of order 4, 5, 6, and 7.

FIG. 9A shows normal incidence reflectance (in an example experiment) for a silver nanocavity 1000 nm long, 60 nm wide, showing resonances of order 4, 5, 6, and 7. Minima in reflectivity correspond to resonances.

Figure 9B:
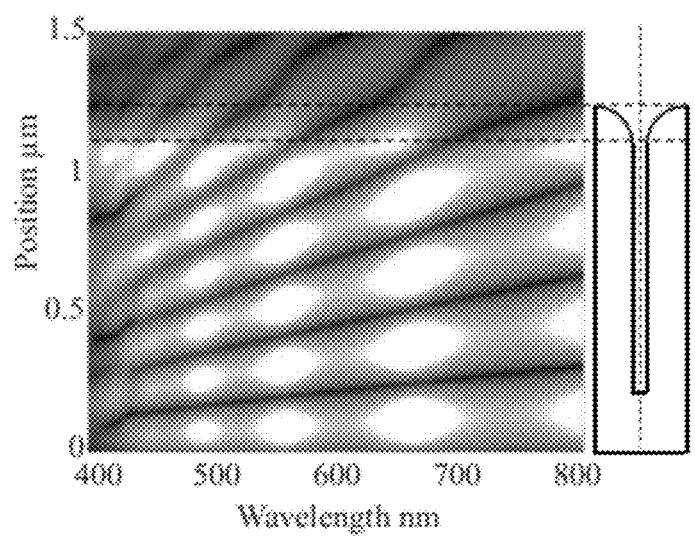
FIG. 9B shows electric field amplitude of the plasmon mode in the center of the plasmon nanocavity plotted as a function of position and excitation wavelength.

FIG. 9B shows electric field amplitude of the plasmon mode in the center of the plasmon nanocavity plotted as a function of position and excitation wavelength. From the continuum of resonant modes, the resonant modes that have a good spatial overlap with the incident photon modes can be optically excited.

The frequency response of the resonator can show strong absorbance peaks that correspond to excitation of high electric field amplitude modes, based on numerical simulation results. Overall absorbance can be extended to other wavelengths by adjusting the length of the resonator such that additional overtones, or resonant modes, can be excited. A longer cavity can result in other frequencies of resonance.

The nanowires can be modeled as vertical cylinders capped by hemispheres sitting on a flat metallic base. The array can be simulated in a rectangular unit cell, of length and width equal to the period of the array and variable height that can depend on the nanowire size. Periodic boundary conditions can be applied along the planes perpendicular to the lattice vectors. The spherical ending of the nanowire can be an effective coupler between the light and the plasmon modes, first because it allows for a large mode overlap between the two, and second because graded separation between the two metallic surfaces can energetically favor focusing of the plasmon mode between the two nanowires in a manner similar to the plasmon energy trap mentioned previously. Compared to other coupling geometries of variable curvature at the end (e.g. a Bezier coefficient, which is a measure of roundness, of 0.01 for cone to 100 for a cylinder) the sphere ranks highest in terms of the absorbance strength of the plasmon resonances.

Calculations were performed for three metals arranged in increasing order of their plasma frequency: gold (2.3 eV), silver (3.8 eV) and aluminum (9.6 eV). A person skilled in the art will be aware that light of a frequency below a plasma frequency can be reflected, because electrons in the metal can screen the electric field of the light, while light of a frequency above the plasma frequency can be transmitted, because the electrons cannot respond fast enough to screen it. Gold can be significant for biomolecular sensing, while silver and aluminum can be relevant for photovoltaic applications since resonances have a better overlap with the solar spectrum.

Figure 10A:
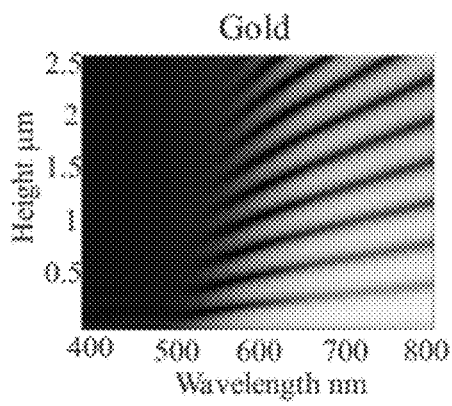
FIG. 10A shows simulations of normal incidence reflected power for gold as a function of wavelength and nanowire height.
Figure 10B:
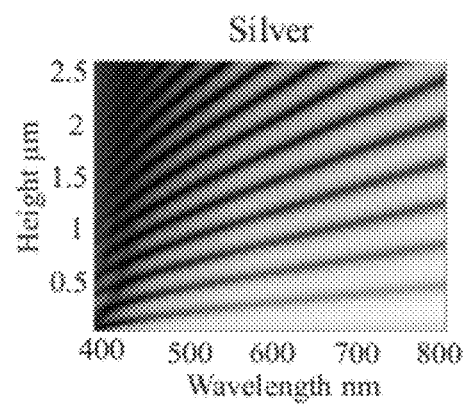
FIG. 10B shows simulations of normal incidence reflected power for silver as a function of wavelength and nanowire height.
Figure 10C:
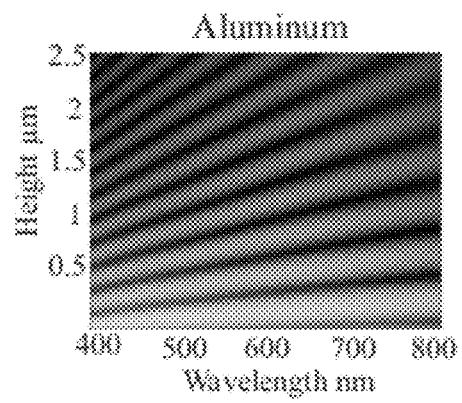
FIG. 10C shows simulations of normal incidence reflected power for aluminum as a function of wavelength and nanowire height.

FIG. 10A shows simulations of normal incidence reflected power for gold as a function of wavelength and nanowire height. FIG. 10B shows simulations of normal incidence reflected power for silver as a function of wavelength and nanowire height. FIG. 10C shows simulations of normal incidence reflected power for aluminum as a function of wavelength and nanowire height. Multiple resonances can be excited below a plasmon cutoff frequency.

Figure 10D:
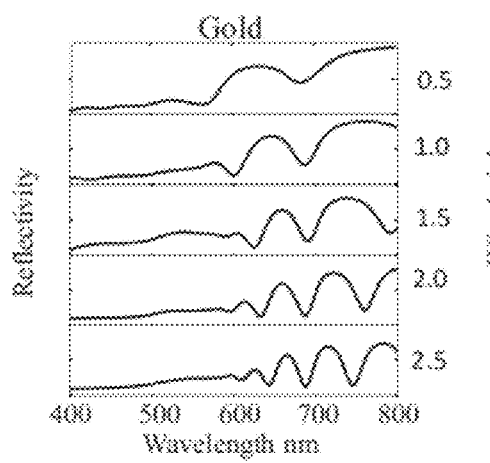
FIG. 10D shows experimental plots of reflectivity for flat metallic films and nanowire arrays of height equal to 0.5, 1, 1.5, 2, and 2.5 μm for gold.
Figure 10E:
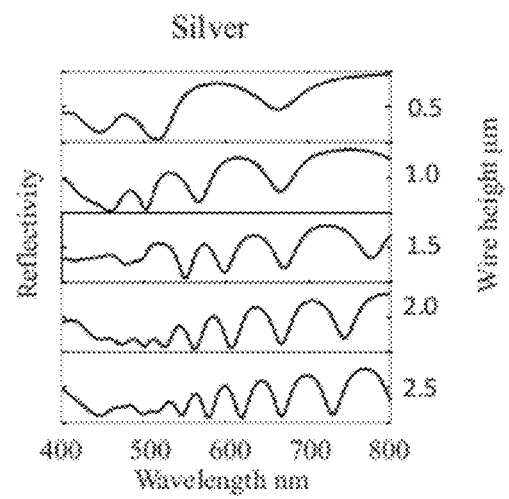
FIG. 10E shows experimental plots of reflectivity for flat metallic films and nanowire arrays of height equal to 0.5, 1, 1.5, 2, and 2.5 μm for silver.
Figure 10F:
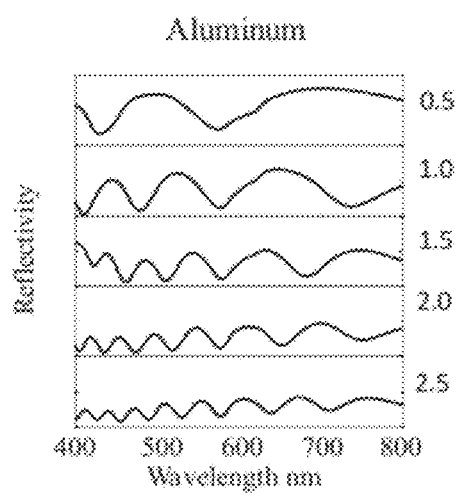
FIG. 10F shows experimental plots of reflectivity for flat metallic films and nanowire arrays of height equal to 0.5, 1, 1.5, 2, and 2.5 μm for aluminum.

FIG. 10D shows experimental plots of reflectivity for flat metallic films and nanowire arrays of height equal to 0.5, 1, 1.5, 2, and 2.5 µm for gold. FIG. 10E shows experimental plots of reflectivity for flat metallic films and nanowire arrays of height equal to 0.5, 1, 1.5, 2, and 2.5 µm for silver. FIG. 10F shows experimental plots of reflectivity for flat metallic films and nanowire arrays of height equal to 0.5, 1, 1.5, 2, and 2.5 µm for aluminum.

Data shown in FIG. 10 correspond to a 360 nm pitch array of vertical nanowires of diameter 310 nm, variable height h, and capped by a hemisphere of diameter 310 nm. At a lowest height the array can be composed of hemispheres alone. The location of the resonances in the near infrared (800 nm) can be approximately the same for all the materials and geometry considered, since the dispersion of plasmons in the near infrared region approaches the dispersion of light in air since infrared light exhibits minimal interaction with metal.

Figure 11A:
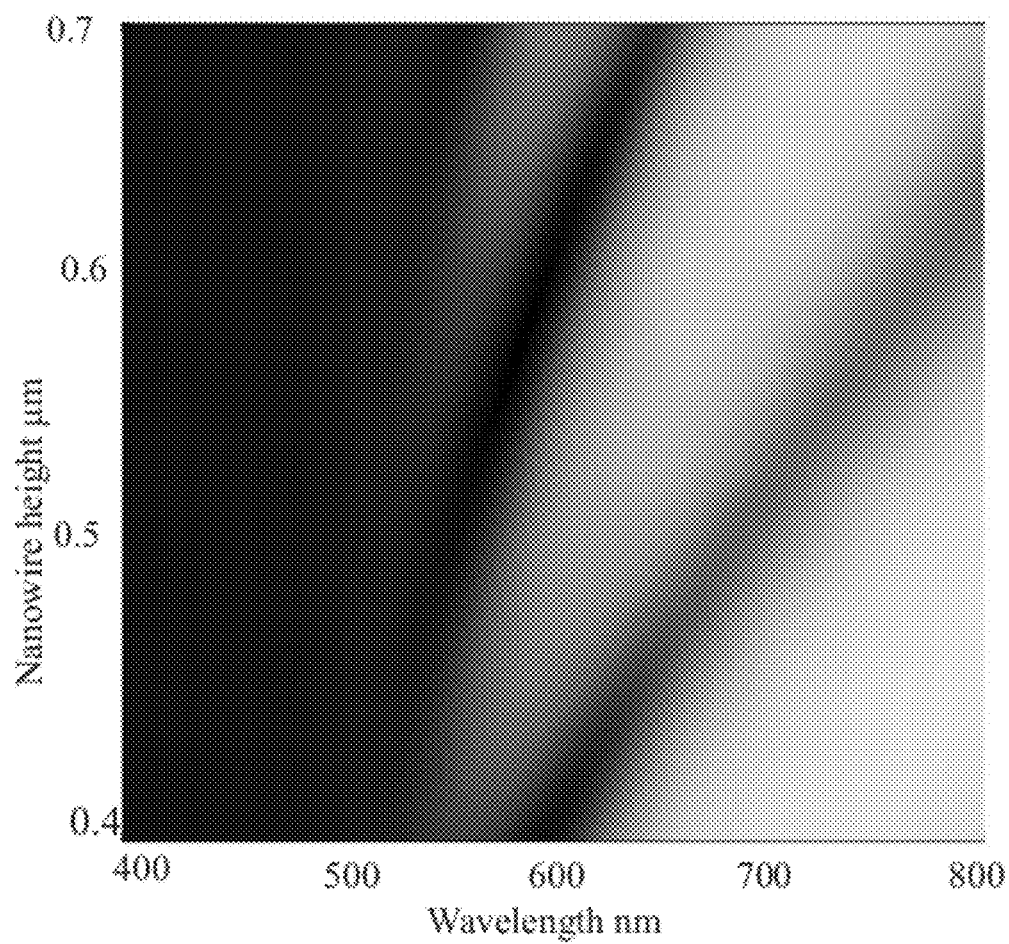
FIG. 11A shows simulation results of the nanowire array reflectivity as a function of wavelength and nanowire height.

FIG. 11A shows simulation results of the nanowire array reflectivity as a function of wavelength and nanowire height. The plasmon resonance can be continuously tuned from 520 to 800 nm.

Figure 11B:
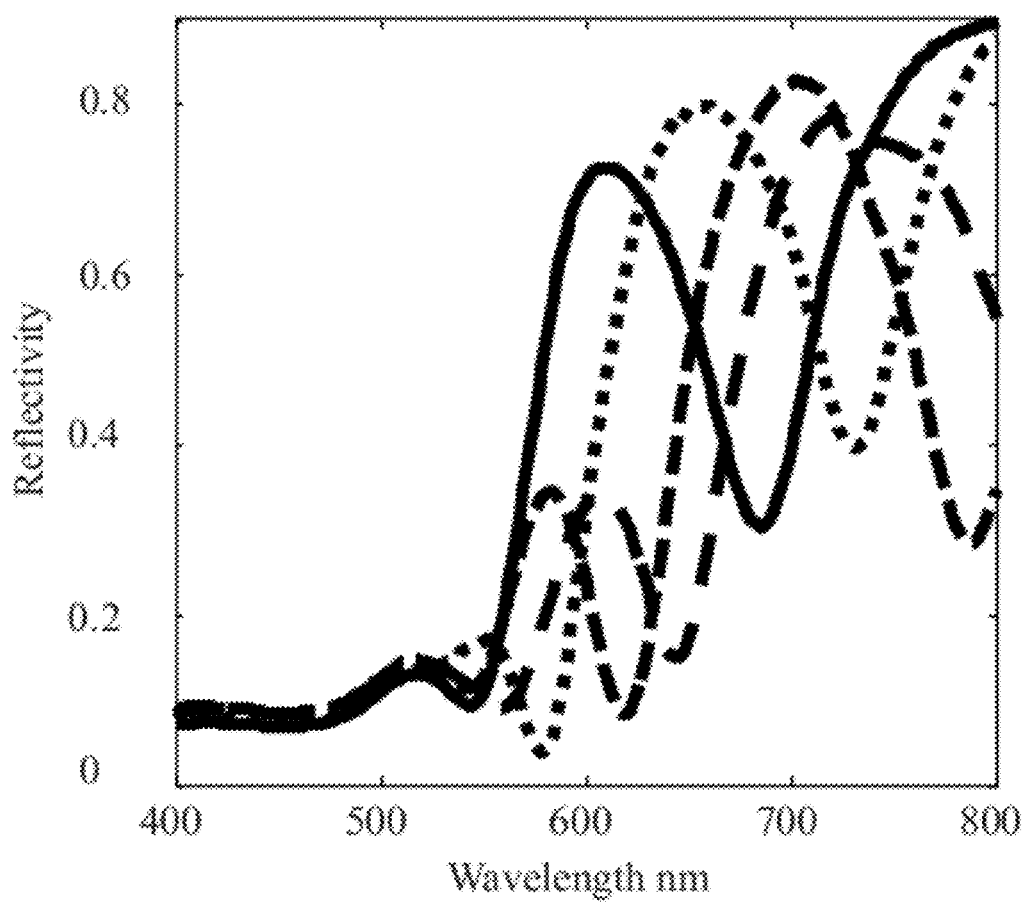
FIG. 11B shows experimental reflectivity for nanowire arrays of diameter 310 nm and height 490 nm (solid), 560 nm (round dot), 620 nm (square dot), and 690 nm (dash).

FIG. 11B shows experimental reflectivity for nanowire arrays of diameter 310 nm and height 490 nm (solid), 560 nm (round dot), 620 nm (square dot), and 690 nm (dash). Examination of FIG. 11A and FIG. 11B reveals that tuning of resonance can be achieved by adjusting nanowire height.

Figure 12:
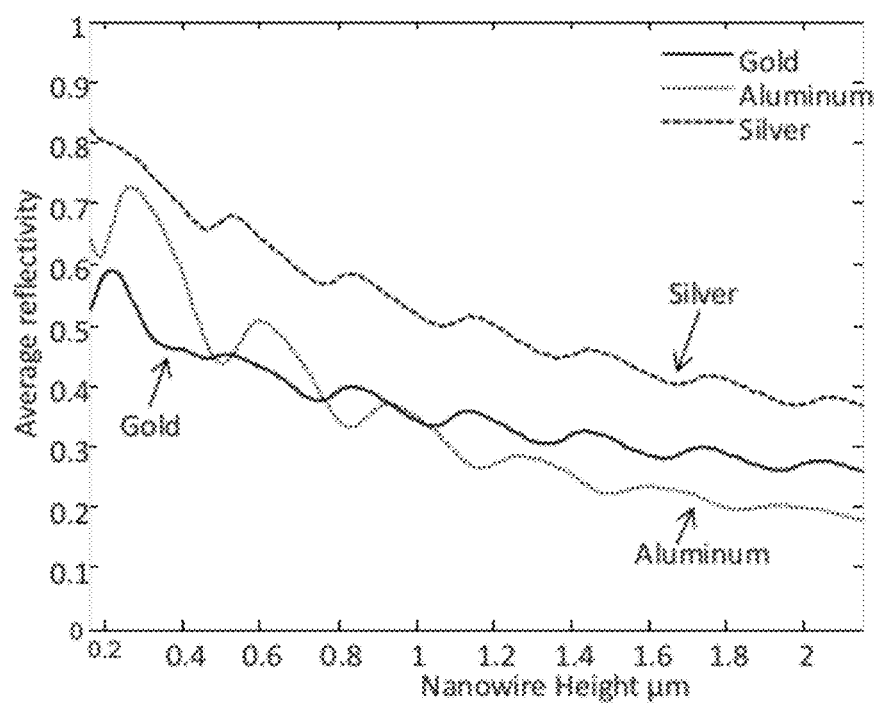
FIG. 12 shows simulated averaged visible reflectivity (400-800 nm) of an array of metallic nanowires as a function of the nanowire height for gold, silver and aluminum.

FIG. 12 shows simulated averaged visible reflectivity (400-800 nm) of an array of metallic nanowires as a function of the nanowire height for gold (red), silver (blue) and aluminum (green). A significant portion of the incident radiation is absorbed in plasmon resonant modes. Tuning of resonance can be achieved by adjusting nanowire height.

Overtone separation (e.g. separation between resonant modes) can be decreased as the excitation light frequency approaches the plasma frequency for each of the metals. Additionally, overtone separation can decrease as length of the resonant cavity increases. In the case of gold only a fraction of the visible spectrum is covered by plasmon resonances as the plasma frequency of gold corresponds to an excitation wavelength of 550 nm, while for silver and aluminum the entire visible spectrum is covered. As the height of the nanowire is increased the spacing between consecutive overtones can decrease, enabling the cavity to have a strong absorbance at more excitation wavelengths. Spacing between each resonance can therefore be reduced by increasing the height of the nanowire. Simulations for the aluminum structures suggest that past a certain height, an increase in the length of the resonator causes a decrease in the absorbance strength. This can be explained by considering the amplitude of the electric field near the excitation end as a superposition of electromagnetic waves travelling the negative and positive direction of the vertical. The end amplitude of the standing wave can be monotonically decreasing with respect to the total absorbance of a round trip inside the resonator such that higher losses in the resonator can correspond to a less efficient coupling with the incident light. Alternatively, the effective length of the resonator can be changed by increasing the refractive index of the dielectric core.

Figure 13A:
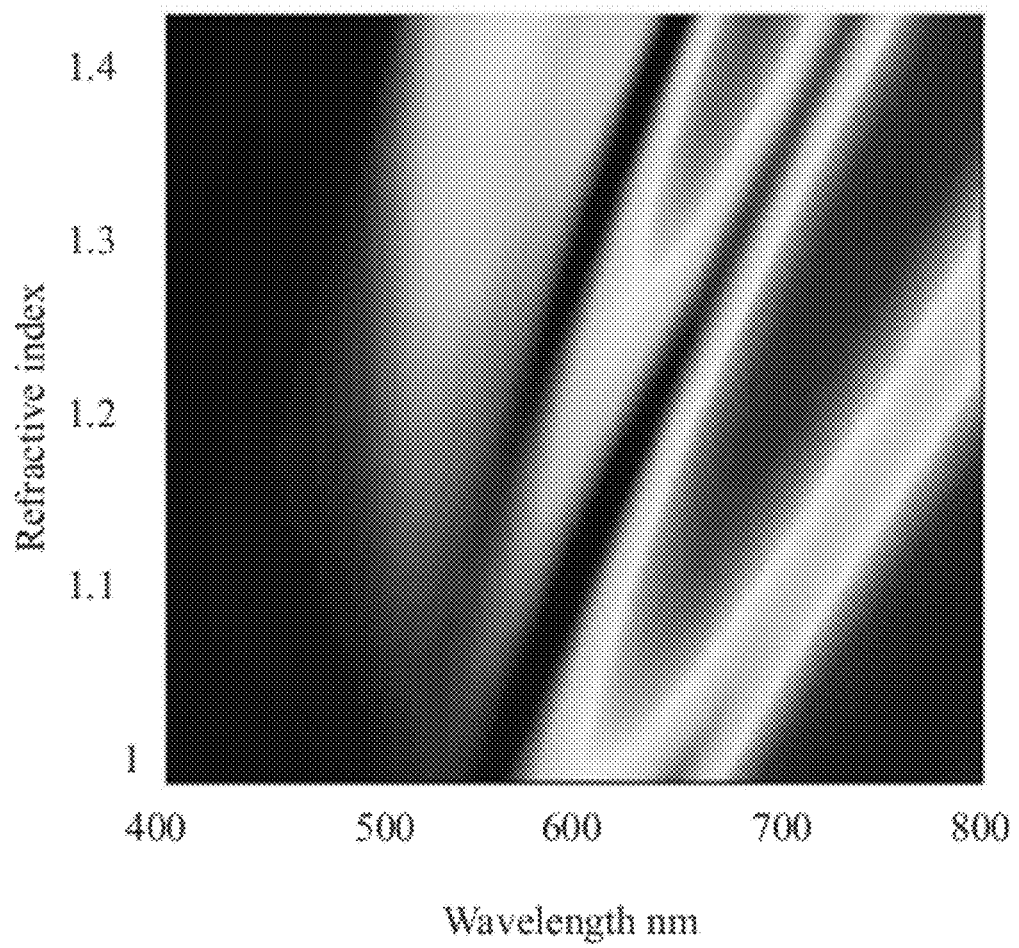
FIG. 13A shows simulation results of the plasmon resonance dependence as a function of dielectric core refractive index for 700 nm tall nanowires.

FIG. 13A shows simulation results of the plasmon resonance dependence as a function of dielectric core refractive index for 700 nm tall nanowires. A red shift of ~450 nm/RIU (refractive index unit) can be observed for all plasmon resonances.

Figure 13B:
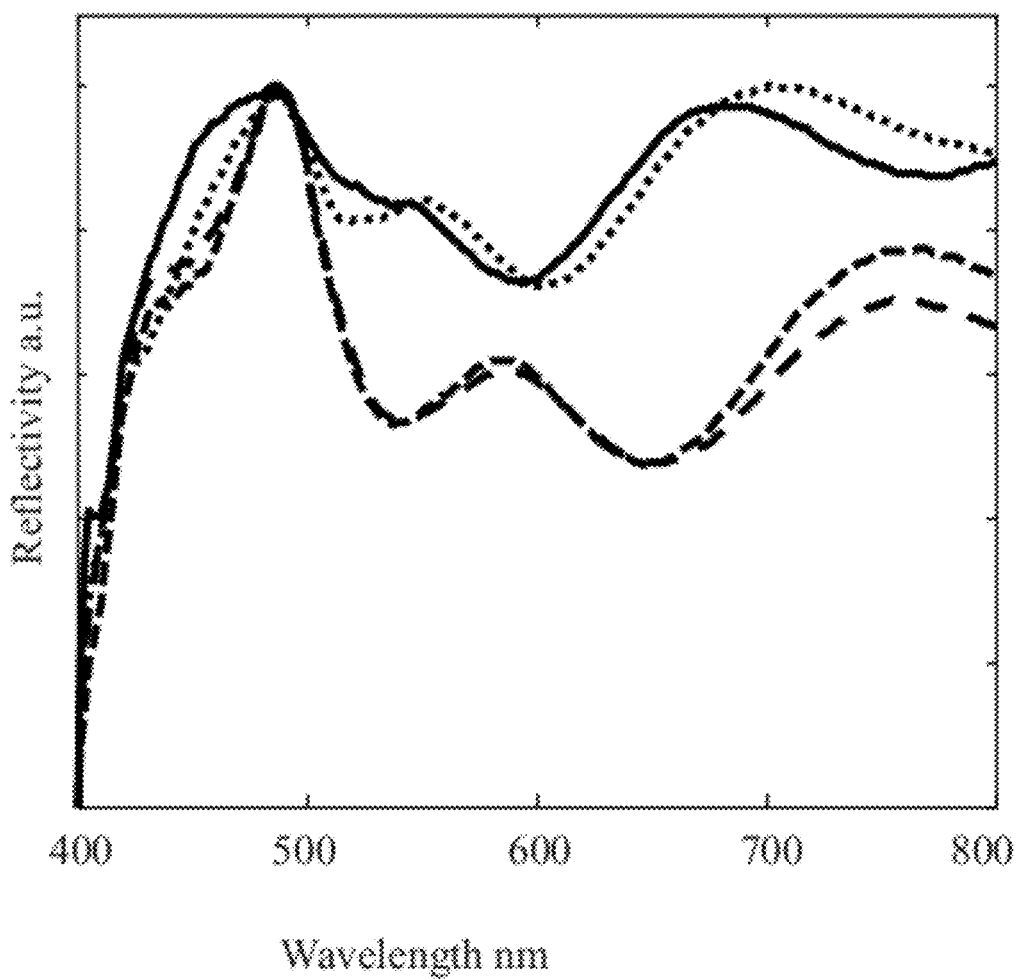
FIG. 13B shows experimental reflectivity plots for array immersion in air (refractive index n=1, solid and round dot) and water (refractive index n=1.33, square dot and dash).

FIG. 13B shows experimental reflectivity plots for array immersion in air (refractive index n=1, solid and round dot) and water (refractive index n=1.33, square dot and dash). Examination of FIG. 13A and FIG. 13B reveals that tuning of resonance can be achieved by adjusting refractive index of a material filling the nanowire cavities.

The examples set forth above are provided to give those of ordinary skill in the art a complete disclosure and description of how to make and use the embodiments of the plasmon resonant cavities in vertical nanowire arrays of the disclosure, and are not intended to limit the scope of what the inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

LIST OF REFERENCES

[1] Hirsch, L. R.; Jackson, J. B.; Lee, A.; Halas, N. J.; West, J., "A Whole Blood Immunoassay Using Gold Nanoshells", Analytical Chemistry 2003, 75, 2377.

[2] Rich, R. L.; Myszka, D. G., "Advances in surface plasmon resonance biosensor analysis", Current Opinion in Biotechnology 2000, 11, 54.

[3] Bora, M.; Celebi, K.; Zuniga, J.; Watson, C.; Milaninia, K. M.; Baldo, M. A., "Near field detector for integrated surface plasmon resonance biosensor applications", Optics Express 2009, 17, 329.

[4] Barnes, W. L.; Dereux, A.; Ebbesen, T. W., "Surface plasmon subwavelength optics", Nature 2003, 424, 824.

[5] Ghaemi, H. F.; Thio, T.; Grupp, D. E.; Ebbesen, T. W.; Lezec, H. J., "Surface plasmons enhance optical transmission through subwavelength holes", Physical Review B 1998, 58, 6779.

[6] Lezec, H. J.; Degiron, A.; Devaux, E.; Linke, R. A.; Martin-Moreno, L.; Garcia-Vidal, F. J.; Ebbesen, T. W., "Beaming Light from a Subwavelength Aperture", Science 2002, 297, 820.

[7] Morfa, A. J.; Rowlen, K. L.; Reilly, T. H.; Romero, M. J.; van de Lagemaat, J., "Surface-plasmon enhanced transparent electrodes in organic photovoltaics", Applied Physics Letters 2008, 92.

[8] Tvingstedt, K.; Persson, N. K.; Inganas, O.; Rahachou, A.; Zozoulenko, I. V., "Surface plasmon increase absorption in polymer photovoltaic cells", Applied Physics Letters 2007, 91.

[9] Westphalen, M.; Kreibig, U.; Rostalski, J.; Luth, H.; Meissner, D., "Metal cluster enhanced organic solar cells", Solar Energy Materials and Solar Cells 2000, 61, 97.

[10] Miyazaki, H. T.; Kurokawa, Y., "Controlled plasmon resonance in closed metal/insulator/metal nanocavities", Applied Physics Letters 2006, 89.

[11] Haynes, C. L.; Van Duyne, R. P., "Nanosphere Lithography: A Versatile Nanofabrication Tool for Studies of Size-Dependent Nanoparticle Optics", Journal of Physical Chemistry B 2001, 105, 5599.

[12] Haynes, C. L.; Van Duyne, R. P., "Plasmon-Sampled Surface-Enhanced Raman Excitation Spectroscopy", Journal of Physical Chemistry B 2003, 107, 7426.

[13] Michaels, A. M.; Nirmal, M.; Brus, L. E., "Surface-Enhanced Raman Spectroscopy of Individual Rhodamine 6G Molecules on Large Ag Nanocrystals", Journal of the American Chemical Society 1999, 121, 9932.

[14] Noginov, M.; Zhu, G.; Belgrave, A.; Bakker, R.; Shalaev, V.; Narimanov, E.; Stout, S.; Herz, E.; Suteewong, T.; Wiesner, U., "Demonstration of a spaser-based nanolaser", Nature 2009, 460, 1110.

[15] Zhang, S.; Berguiga, L.; Elezgaray, J.; Roland, T.; Faivre-Moskalenko, C.; Argoul, F., "Surface plasmon resonance characterization of thermally evaporated thin gold films", Surf. Sci. 2007, 601, 5445.

[16] Manjavacas, A.; de Abajo, F. J. G., "Robust Plasmon Waveguides in Strongly Interacting Nanowire Arrays", Nano Letters 2009, 9, 1285.

[17] Manjavacas, A.; de Abajo, F. J. G., "Coupling of gap plasmons in multi-wire waveguides", Optics Express 2009, 17, 19401.

[18] Stegeman, G. I.; Wallis, R. F.; Maradudin, A. A., "Excitation of surface polaritons by end-fire coupling", Optics Letters 1983, 8, 386.

[19] Fernandez, A.; Nguyen, H. T.; Britten, J. A.; Boyd, R. D.; Perry, M. D.; Kania, D. R.; Hawryluk, A. M., "Use of interference lithography to pattern arrays of submicron resist structures for field emission flat panel displays", Journal of Vacuum Science & Technology B 1997, 15, 729.

[20] Dionne, J. A.; Sweatlock, L. A.; Atwater, H. A.; Polman, A., "Plasmon slot waveguides: towards chip-scale propagation with sub-wavelength scale localization", Physical Review B 2006, 73.

[21] Lezec, H. J.; Dionne, J. A.; Atwater, H. A., "Negative Refraction at Visible Frequencies", Science 2007, 316, 430.

[22] Prodan, E.; Radloff, C.; Halas, N. J.; Nordlander, P., "A Hybridization Model for the Plasmon Response of Complex Nanostructures", Science 2003, 302, 419.

[23] Sun, Z. J.; Zeng, D. Y., "Coupling of Surface Plasmon Waves in Metal/Dielectric Gap Waveguides and Single Interface Waveguides", Journal of the Optical Society of America B-Optical Physics 2007, 24, 2883.

[24] Johnson, P. B.; Christy, R. W., "Optical Constants of the Noble Metals", Physical Review B 1972, 6, 4370.

The invention claimed is:

1. A plasmonic structure comprising:
    a planar substrate; and
    an array of metal-coated dielectric cylindrical nanowires, the cylindrical nanowires being aligned along two mutually perpendicular directions and being end-connected substantially orthogonally to the planar substrate so that plasmon resonant gap-cavities capable of supporting propagation of gap plasmon modes are formed between adjacent pairs of said nanowires with one end of each of said plasmon resonant gap-cavities delimited by a surface of the planar substrate and another end of each of said plasmon resonant gap-cavities open ended,
    wherein the cavities are capable of supporting gap plasmon modes excited by light normally incident on an open end side of the cavities.

2. The plasmonic structure of claim 1,
    wherein said nanowires are tuned to have a set aspect ratio and spacing so that said plasmon resonant gap-cavities are tuned to have a predetermined longitudinal length and width for a predetermined plasmon wavelength and a predetermined cavity order.

3. The plasmonic structure of claim 1,
    wherein the delimiting surface of the planar substrate is a reflective surface.

4. The plasmonic structure of claim 1,
    wherein said nanowires taper to a reduced diameter at the open ends of the plasmon resonant gap-cavities.

5. The plasmonic structure of claim 4,
    wherein said nanowires have substantially hemispherical caps at the open ends.

6. The plasmonic structure of claim 1,
    wherein said plasmon resonant gap-cavities have a width measured between said adjacent pairs of nanowires that is less than about 50 nm.

7. The plasmonic structure of claim 1,
    wherein said plasmon resonant gap-cavities have a length measured between said delimited and open ends that is substantially an odd multiple of quarter plasmon wavelengths.

8. The plasmonic structure of claim 1,
    further comprising a photovoltaic material filling said plasmon resonant gapcavities.

9. The plasmonic structure of claim 1,
    further comprising an active gain medium filling said plasmon resonant gapcavities.

10. The plasmonic structure of claim 1,
    wherein said planar substrate is a silica substrate, and said metal-coated dielectric nanowires are gold-coated silica nanowires with an intermediate alumina layer between the silica and the gold coating.

11. A method of fabricating a plasmonic structure comprising:
- providing a planar dielectric substrate;
- producing an etch pattern on the planar dielectric substrate;
- etching the planar dielectric substrate based on the etch pattern to produce an array of dielectric cylindrical nanowires end-connected substantially orthogonally to the planar dielectric substrate and in parallel arrangement with each other, and
- coating the dielectric nanowires with a metallic outer layer so that plasmon resonant gap-cavities capable of supporting propagation of gap plasmon modes are formed between adjacent pairs of said nanowires with one end of each of said plasmon resonant gap-cavities delimited by a surface of the planar substrate and another end of each of said plasmon resonant gap-cavities open ended, the plasmon resonant gap-cavities being configured to support gap plasmon modes excited by light normally incident on an open end side of the plasomon resonant gap-cavities.

12. The method of claim 11,
wherein the step of coating the dielectric nanowires includes depositing the metallic outer layer so that resulting coated nanowires are tuned to have a set aspect ratio and spacing, and so that the plasmon resonant gapcavities are tuned to have a predetermined longitudinal length and width for a predetermined plasmon wavelength and predetermined cavity order.

13. The method of claim 11,
further comprising forming a reflective surface on the delimiting surface of the planar substrate.

14. The method of claim 11,
further comprising tapering said nanowires at the open ends of the plasmon resonant gap-cavities to a reduced diameter.

15. The method of claim 14,
further comprising tapering said nanowires at the open ends of the plasmon resonant gap-cavities to have substantially hemispherical caps at the open ends.

16. The method of claim 11,
wherein said dielectric nanowires are coated with the metallic outer layer so that a width of each plasmon resonant gap-cavity measured between adjacent pairs of coated nanowires is less than about 50 nm.

17. The method of claim 11,
wherein the planar dielectric substrate is etched a predetermined etch depth so that a length of each plasmon resonant gap-cavity measured between the delimited and open ends is substantially an odd multiple of quarter plasmon wavelengths.

18. The method of claim 11,
further comprising filling said plasmon resonant gap-cavities with a photovoltaic material.

19. The method of claim 11,
further comprising filling said plasmon resonant gap-cavities with an active gain medium.

20. The method of claim 11,
further comprising forming an intermediate oxide layer between the etched dielectric nanowires and the metallic outer layer.

21. The plasmonic structure of claim 1,
wherein at least some of the cylindrical nanowires are surrounded by four cylindrical nanowires defining four resonant cavities associated to each surrounded nanowire.

22. The plasmonic structure of claim 1,
wherein the plasmon resonant gap-cavities in the array of metal-coated dielectric cylindrical nanowires have a density of $3.85*10^8$ cavities/cm$^2$.

23. The plasmonic structure of claim 1,
wherein the cylindrical nanowires are configured to concentrate 90% of total electromagnetic field energy in a circular sector of the cylindrical nanowire, the circular sector having a ±12 degrees opening.

24. The plasmonic structure of claim 1,
wherein a center-to-center distance between nanowires in the array is 360 nm and an edge to edge wire distance is 15-35 nm.

25. The method of claim 11,
wherein the step of coating the dielectric nanowires includes depositing a 20-40 nm thick metallic outer layer until an edge to edge distance between adjacent nanowires approaches 20-40 nm.

* * * * *